(12) United States Patent
Walker et al.

(10) Patent No.: US 12,162,911 B2
(45) Date of Patent: *Dec. 10, 2024

(54) PULMONARY ADMINISTRATION OF PYOCINS FOR TREATING BACTERIAL RESPIRATORY INFECTIONS

(71) Applicant: The University Court of the University of Glasgow, Glasgow Strathclyde (GB)

(72) Inventors: Daniel Walker, Glasgow Strathclyde (GB); Laura McCaughey, Glasgow Strathclyde (GB)

(73) Assignee: The University Court Of tThe University of Glasgow, Glasgow Strathclyde (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/173,333

(22) Filed: Feb. 23, 2023

(65) Prior Publication Data

US 2023/0303636 A1 Sep. 28, 2023

Related U.S. Application Data

(63) Continuation of application No. 15/512,548, filed as application No. PCT/EP2015/071768 on Sep. 22, 2015, now Pat. No. 11,643,442.

(30) Foreign Application Priority Data

Sep. 23, 2014 (GB) ..................................... 1416788

(51) Int. Cl.
| | |
|---|---|
| *C07K 14/21* | (2006.01) |
| *A61K 38/16* | (2006.01) |
| *A61K 9/00* | (2006.01) |
| *A61K 38/00* | (2006.01) |

(52) U.S. Cl.
CPC ............ *C07K 14/21* (2013.01); *A61K 38/164* (2013.01); *A61K 9/0073* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 7,700,729 B2* | 4/2010 | Scholl ..................... | C07K 14/21 | |
| | | | 435/69.7 | |
| 2003/0113293 A1* | 6/2003 | Bermudes .............. | A61K 48/00 | |
| | | | 424/93.2 | |
| 2006/0229244 A1 | 10/2006 | Dorit | | |
| 2008/0113406 A1* | 5/2008 | Martin ..................... | C07K 14/21 | |
| | | | 536/23.7 | |
| 2008/0286236 A1 | 11/2008 | Gebhart | | |
| 2010/0183655 A1* | 7/2010 | Swartz ..................... | C07K 16/00 | |
| | | | 424/190.1 | |
| 2014/0050713 A1* | 2/2014 | Appaiah ............... | C12N 9/2462 | |
| | | | 424/94.3 | |

FOREIGN PATENT DOCUMENTS

| | | |
|---|---|---|
| JP | 2001505557 | 4/2001 |
| JP | 3655645 B2 | 6/2005 |
| WO | 9820836 | 5/1998 |
| WO | WO98020836 | 5/1998 |

OTHER PUBLICATIONS

Greene, Catherine et al. Proteases and antiproteases in chronic neutrophilic lung disease—relevance to drug discovery. British Journal of Pharmacology (2009), 158, 1048-1058. (Year: 2009).*
Matthews, Abigail et al. Developing inhaled protein therapeutics for lung diseases. Molecular Biomedicine. Springer. pp. 1-11. (Year: 2020).*
Naz, Sehar et al. Biophysicochemical characterization of Pyocin SA189 produced by Pseudomonas aeruginosa SA189. Brazilian Journal of Microbiology 46, 4. pp. 1147-1154. (Year: 2015).*
Karaboga, Enes. S-pyocins as potential antimicrobials reagents for eradicating Pseudomonas aeruginosa biofilms. Sabanci University. (Year: 2014).*
Hirche, Tim et al. Neutrophil Elastase Mediates Innate Host Protection against Pseudomonas aeruginosa. The Journal of Immunology. 181. pp. 4945-4954. (Year: 2008).*
"Bacteriocin", Wikipedia, retrived from the internet at: https://en.wikipedia.org/wiki/Bacteriocin on Jan. 17, 2020.
Elfarash (Pore-forming pyocin S5 utilizes the FptA ferripyochelin receptor to kill Pseudomonas aeruginosa, 2014 ) (Year: 2014).
Greene, Catherine, et al., "Themed Section: Mediators and Receptors in the Resolution of Inflammation", British Journal of Pharacology (2009), 158, 1048-1058.
Hector, Andreas, et al., "In Vitro Inhibition of Neutrophil Elastase Activity by Inhaled Anti-Pseudomonas Antibiotics Used in Cystic Fibrosis Patients", Mediators of Inflammation, vol. 2010, Article ID 809591, 5 pgs.
Hirche et al., "Protection against Pseudomonas aeruginosa Neutrophil Elastase Mediates Innate Host", J. Immunol., 2008, 181:4945-4954.
Jones, A., et al., "Colistin stimulates the activity of neutrophil elastase and Pseudomonas aeruginosa elastase", European Respiratory Journal, 2002; 19: 1136-1141.

(Continued)

*Primary Examiner* — Nghi V Nguyen

(74) *Attorney, Agent, or Firm* — FisherBroyles, LLP; Adam K. Whiting; Adelaide K. Leitzel

(57) ABSTRACT

The treatment of bacterial respiratory infections using bacterially-originating antibiotics known as pyocins are provided. In particular, S-type pyocins are administered by pulmonary administration for the treatment of bacterial infections such as *Pseudomonas aeruginosa* infections. Methods of using S-type pyocin proteins, particularly those comprising an S2, SD2, S5 or AP41 targeting portion or an S2, SD2, S5 or AP41 effector portion are provided.

16 Claims, 4 Drawing Sheets

Specification includes a Sequence Listing.

(56) References Cited

OTHER PUBLICATIONS

Kawabata et al., "The role of neutrophil elastase in acute lung injury", European Journal of Pharmacology, 2002, 451:1-10.
Koeppen, Katja, et al., "Tobramycin reduces key virulence determinants in the proteome of Pseudomonas aeruginosa outer membrane vesicles", PLOS One, https:/doi.org/10.1371/journal.pone.0211290; Jan. 25, 2019, 14 pgs.
Lavoie et al., "Innate immune responses to Pseudomonas aeruginosa infection", Microbes Infect., 2011, 13(14-15): 1133-1145.
Matthews, Abigail A., et al., "Developing inhaled protein therapeutics for lung diseases", Department of Biological Sciences, Faculty of Science, National University of Singapore, Molecular Biomedicine (2020) 1:11.
Morita, Takahiro, et al., "Drug Delivery System", Department of Basic Pharmaceutics, Kyoto University, 1991, vol. 6, No. 3, pp. 207-211.
Okamoto, Hirokazu, et al., "Local and Systemic Delivery of High-Molecular Weight Drugs by Powder Inhalation", Journal of the Pharmaceutical Society of Japan, 2007, vol. 127, No. 4, 643-653.
Smith, Karen et al.Activity of Pyocin S2 against Pseudomonas aeruginous Biofilms. Antimicrob Agents Chemother. (2012) 56, 1599-1601. (Year: 2012).
Wojda, Iwona, et al., "The greater wax moth Galleria mellonella: biology and use in immune studies", Oxford FEMS, Pathogens and Disease, 78, 2020, ftaa057; Sep. 24, 2020.
Brown et al., "Colicin-like bacteriocins as novel therapeutic agents for the treatment of chronic biofilm-mediated Infection", Biochemical Society Transactions, (Nov. 21, 2012), vol. 7, No. 6, doi:10.3748/wjg.v17.i14.1797, ISSN 0300-5127, pp. 521-1552, XP055079887.
Elfarash A et al, "Pore-forming pyocin S5 utilizes the FptA ferripyochelin receptor to kill Pseudomonas aeruginosa", Microbiology (United Kingdom) Feb. 2014 Society for General Microbiology GBR, (Feb. 2014), vol. 160, No. Part 2, ISSN 1350-0872, pp. 261-269, XP002751102.
Hua Ling et al, "A predicted S-type pyocin shows a bactericidal activity against clinicalisolates through membrane damage", FEBS Letters, Elsevier, Amsterdam, NL, vol. 584, No. 15, doi:10.1016/J.FEBSLET.2010.06.021, ISSN 0014-5793, (Jun. 14, 2010), pp. 3354-3358, (Ju. 18, 2010), XP028340497.
Scholl Dean et al, "Antibacterial efficacy of R-type pyocins towards Pseudomonas aeruginosa in a murine peritonitis model", Antimicrobial Agents and Chemotherapy, (May 2008), vol. 52, No. 5, ISSN 0066-4804, pp. 1647-1652, XP002751100.
De Kwaadsteniet M et al, "Nisin F in the treatment of respiratory tract infections caused by *Staphylococcus aureus* ", Letters in Applied Microbiology, (Jan. 2009), vol. 48, No. 1, ISSN 0266-8254, pp. 65-70, XP002751101.
Michael-Brand, Yyon et al, "The pyocins of Pseudomonas aeruginosa", Biochimie 84 (2002) 499-510.
Behrens, Hannah M., et al. "Pyocin S5 import into Pseudomonas aeruginosa reveals a generic mode of bacteriocin transport." MBio 11.2 (2020): 10-1128.

\* cited by examiner

SEQUENCE LISTING

```
Sequence total quantity: 40
SEQ ID NO: 1           moltype = AA  length = 689
FEATURE                Location/Qualifiers
source                 1..689
                       mol_type = protein
                       organism = Pseudomonas aeruginosa
SEQUENCE: 1
MAVNDYEPGS MVITHVQGGG RDIIQYIPAR SSYGTPPFVP PGPSPYVGTG MQEYRKLRST   60
LDKSHSELKK NLKNETLKEV DELKSEAGLP GKAVSANDIR DEKSIVDALM DAKAKSLKAI  120
EDRPANLYTA SDFPQKSESM YQSQLLASRK FYGEFLDRHM SELAKAYSAD IYKAQIAILK  180
QTSQELENKA RSLEAEAQRA AAEVEADYKA RKANVEKKVQ SELDQAGNAL PQLTNPTPEQ  240
WLERATQLVT QAIANKKKLQ TANNALIAKA PNALEKQKAT YNADLLVDEI ASLQARLDKL  300
NAETARRKEI ARQAAIRAAN TYAMPANGSV VATAAGRGLI QVAQGAASLA QAISDAIAVL  360
```

```
GRVLASAPSV MAVGFASLTY SSRTAEQWQD QTPDSVRYAL GMDAAKLGLP PSVNLNAVAK    420
ASGTVDLPMR LTNEARGNTT TLSVVSTDGV SVPKAVPVRM AAYNATTGLY EVTVPSTTAE    480
APPLILTWTP ASPPGNQNPS STTPVVPKPV PVYEGATLTP VKATPETYPG VITLPEDLII    540
GFPADSGIKP IYVMFRDPRD VPGAATGKGQ PVSGNWLGAA SQGEGAPIPS QIADKLRGKT    600
FKNWRDFREQ FWIAVANDPE LSKQFNPGSL AVMRDGGAPY VRESEQAGGR IKIEIHHKVR    660
IADGGGVYNM GNLVAVTPKR HIEIHKGGK                                     689

SEQ ID NO: 2            moltype = AA  length = 558
FEATURE                 Location/Qualifiers
source                  1..558
                        mol_type = protein
                        organism = Pseudomonas aeruginosa
SEQUENCE: 2
MAVNDYEPGS MVITHVQGGG RDIIQYIPAR SSYGTPPFVP PGPSPYVGTG MQEYRKLRST     60
LDKSHSELKK NLKNETLKEV DELKSEAGLP GKAVSANDIR DEKSIVDALM DAKAKSLKAI    120
EDRPANLYTA SDFPQKSESM YQSQLLASRK FYGEFLDRHM SELAKAYSAD IYKAQIAILK    180
QTSQELENKA RSLEAEAQRA AAEVEADYKA RKANVEKKVQ SELDQAGNAL PQLTNPTPEQ    240
WLERATQLVT QAIANKKKLQ TANNALIAKA PNALEKQKAT YNADLLVDEI ASLQARLDKL    300
NAETARRKEI ARQAAIRAAN TYAMPANGSV VATAAGRGLI QVAQGAASLA QAISDAIAVL    360
GRVLASAPSV MAVGFASLTY SSRTAEQWQD QTPDSVRYAL GMDAAKLGLP PSVNLNAVAK    420
ASGTVDLPMR LTNEARGNTT TLSVVSTDGV SVPKAVPVRM AAYNATTGLY EVTVPSTTAE    480
APPLILTWTP ASPPGNQNPS STTPVVPKPV PVYEGATLTP VKATPETYPG VITLPEDLII    540
GFPADSGIKP IYVMFRDP                                                 558

SEQ ID NO: 3            moltype = AA  length = 216
FEATURE                 Location/Qualifiers
source                  1..216
                        mol_type = protein
                        organism = Pseudomonas aeruginosa
SEQUENCE: 3
MAVNDYEPGS MVITHVQGGG RDIIQYIPAR SSYGTPPFVP PGPSPYVGTG MQEYRKLRST     60
LDKSHSELKK NLKNETLKEV DELKSEAGLP GKAVSANDIR DEKSIVDALM DAKAKSLKAI    120
EDRPANLYTA SDFPQKSESM YQSQLLASRK FYGEFLDRHM SELAKAYSAD IYKAQIAILK    180
QTSQELENKA RSLEAEAQRA AAEVEADYKA RKANVE                             216

SEQ ID NO: 4            moltype = AA  length = 96
FEATURE                 Location/Qualifiers
source                  1..96
                        mol_type = protein
                        organism = Pseudomonas aeruginosa
SEQUENCE: 4
KKVQSELDQA GNALPQLTNP TPEQWLERAT QLVTQAIANK KKLQTANNAL IAKAPNALEK     60
QKATYNADLL VDEIASLQAR LDKLNAETAR RKEIAR                              96

SEQ ID NO: 5            moltype = AA  length = 245
FEATURE                 Location/Qualifiers
source                  1..245
                        mol_type = protein
                        organism = Pseudomonas aeruginosa
SEQUENCE: 5
AAIRAANTYA MPANGSVVAT AAGRGLIQVA QGAASLAQAI SDAIAVLGRV LASAPSVMAV     60
GFASLTYSSR TAEQWQDQTP DSVRYALGMD AAKLGLPPSV NLNAVAKASG TVDLPMRLTN    120
EARGNTTTLS VVSTDGVSVP KAVPVRMAAY NATTGLYEVT VPSTTAEAPP LILTWTPASP    180
PGNQNPSSTT PVVPKPVPVY EGATLTPVKA TPETYPGVIT LPEDLIIGFP ADSGIKPIYV    240
MFRDP                                                               245

SEQ ID NO: 6            moltype = AA  length = 131
FEATURE                 Location/Qualifiers
source                  1..131
                        mol_type = protein
                        organism = Pseudomonas aeruginosa
SEQUENCE: 6
RDVPGAATGK GQPVSGNWLG AASQGEGAPI PSQIADKLRG KTFKNWRDFR EQFWIAVAND     60
PELSKQFNPG SLAVMRDGGA PYVRESEQAG GRIKIEIHHK VRIADGGGVY NMGNLVAVTP    120
KRHIEIHKGG K                                                        131

SEQ ID NO: 7            moltype = AA  length = 662
FEATURE                 Location/Qualifiers
source                  1..662
                        mol_type = protein
                        organism = Pseudomonas aeruginosa
SEQUENCE: 7
MAVNDYEPGS MVITHVQGGG RDIIQYIPAR SSYGTPPFVP PGPSPYVGTG MQEYRKLRST     60
LDKSHSELKK NLKNETLKEV DELKSEAGLP GKAVSANDIR DEKSIVDALM DAKAKSLKAI    120
EDRPANLYTA SDFPQKSESM YQSQLLASRK FYGEFLDRHM SELAKAYSAD IYKAQIAILK    180
QTSQELENKA RSLEAEAQRA AAEVEADYKA RKANVEKKVQ SELDQAGNAL PQLTNPTPEQ    240
WLERATQLVT QAIANKKKLQ TANNALIAKA PNALEKQKAT YNADLLVDEI ASLQARLDKL    300
NAETARRKEI ARQAAIRAAN TYAMPANGSV VATAAGRGLI QVAQGAASLA QAISDAIAVL    360
GRVLASAPSV MAVGFASLTY SSRTAEQWQD QTPDSVRYAL GMDANKLGLT SSVNLSAVAK    420
```

```
AGGTVDLPMR LTNEARGNTT TLSVVSTDGV SVPKAAPVRM AAYNATTGLY EVTVPSTTAE   480
APPLILTWTP ASPPGNQNPS STTPVIPKPV PVYEGAALTP LKTGPESYPG MLLDLNDLIV   540
IFPADSGVKP VYVMLSSPLD SGIFTRRQLQ KKFDSHKYDF GLGEKSANNG TLAEFRDKIL   600
EHLADPATVE KGTYHSEVNS KVHYNARTNI VVIIGEDGMF VSGWRIEPGT DQYNFYMKNE   660
VL                                                                662

SEQ ID NO: 8            moltype = AA  length = 554
FEATURE                 Location/Qualifiers
source                  1..554
                        mol_type = protein
                        organism = Pseudomonas aeruginosa
SEQUENCE: 8
MAVNDYEPGS MVITHVQGGG RDIIQYIPAR SSYGTPPFVP PGPSPYVGTG MQEYRKLRST    60
LDKSHSELKK NLKNETLKEV DELKSEAGLP GKAVSANDIR DEKSIVDALM DAKAKSLKAI   120
EDRPANLYTA SDFPQKSESM YQSQLLASRK FYGEFLDRHM SELAKAYSAD IYKAQIAILK   180
QTSQELENKA RSLEAEAQRA AAEVEADYKA RKANVEKKVQ SELDQAGNAL PQLTNPTPEQ   240
WLERATQLVT QAIANKKKLQ TANNALIAKA PNALEKQKAT YNADLLVDEI ASLQARLDKL   300
NAETARRKEI ARQAAIRAAN TYAMPANGSV VATAAGRGLI QVAQGAASLA QAISDAIAVL   360
GRVLASAPSV MAVGFASLTY SSRTAEQWQD QTPDSVRYAL GMDANKLGLT SSVNLSAVAK   420
AGGTVDLPMR LTNEARGNTT TLSVVSTDGV SVPKAAPVRM AAYNATTGLY EVTVPSTTAE   480
APPLILTWTP ASPPGNQNPS STTPVIPKPV PVYEGAALTP LKTGPESYPG MLLDLNDLIV   540
IFPADSGVKP VYVM                                                   554

SEQ ID NO: 9            moltype = AA  length = 216
FEATURE                 Location/Qualifiers
source                  1..216
                        mol_type = protein
                        organism = Pseudomonas aeruginosa
SEQUENCE: 9
MAVNDYEPGS MVITHVQGGG RDIIQYIPAR SSYGTPPFVP PGPSPYVGTG MQEYRKLRST    60
LDKSHSELKK NLKNETLKEV DELKSEAGLP GKAVSANDIR DEKSIVDALM DAKAKSLKAI   120
EDRPANLYTA SDFPQKSESM YQSQLLASRK FYGEFLDRHM SELAKAYSAD IYKAQIAILK   180
QTSQELENKA RSLEAEAQRA AAEVEADYKA RKANVE                            216

SEQ ID NO: 10           moltype = AA  length = 96
FEATURE                 Location/Qualifiers
source                  1..96
                        mol_type = protein
                        organism = Pseudomonas aeruginosa
SEQUENCE: 10
KKVQSELDQA GNALPQLTNP TPEQWLERAT QLVTQAIANK KKLQTANNAL IAKAPNALEK    60
QKATYNADLL VDEIASLQAR LDKLNAETAR RKEIAR                             96

SEQ ID NO: 11           moltype = AA  length = 242
FEATURE                 Location/Qualifiers
source                  1..242
                        mol_type = protein
                        organism = Pseudomonas aeruginosa
SEQUENCE: 11
QAAIRAANTY AMPANGSVVA TAAGRGLIQV AQGAASLAQA ISDAIAVLGR VLASAPSVMA    60
VGFASLTYSS RTAEQWQDQT PDSVRYALGM DANKLGLTSS VNLSAVAKAG GTVDLPMRLT   120
NEARGNTTTL SVVSTDGVSV PKAAPVRMAA YNATTGLYEV TVPSTTAEAP PLILTWTPAS   180
PPGNQNPSST TPVIPKPVPV YEGAALTPLK TGPESYPGML LDLNDLIVIF PADSGVKPVY   240
VM                                                                242

SEQ ID NO: 12           moltype = AA  length = 108
FEATURE                 Location/Qualifiers
source                  1..108
                        mol_type = protein
                        organism = Pseudomonas aeruginosa
SEQUENCE: 12
LSSPLDSGIF TRRQLQKKFD SHKYDFGLGE KSANNGTLAE FRDKILEHLA DPATVEKGTY    60
HSEVNSKVHY NARTNIVVII GEDGMFVSGW RIEPGTDQYN FYMKNEVL                108

SEQ ID NO: 13           moltype = AA  length = 498
FEATURE                 Location/Qualifiers
source                  1..498
                        mol_type = protein
                        organism = Pseudomonas aeruginosa
SEQUENCE: 13
MSNDNEVPGS MVIVAQGPDD QYAYEVPPID SAAVAGNMFG DLIQREIYLQ KNIYYPVRSI    60
FEQGTKEKKE INKKVSDQVD GLLKQITQGK REATRQERVD VMSAVLHKME SDLEGYKKTF   120
TKGPFIDYEK QSSLSIYEAW VKIWEKNSWE ERKKYPFQQL VRDELERAVA YYKQDSLSEA   180
VKVLRQELNK QKALKEKEDL SQLERDYRTR KANLEMKVQS ELDQAGSALP PLVSPTPEQW   240
LERATRLVTQ AIADKKQLQT TNNTLIKNSP TPLEKQKAIY NGELLVDEIA SLQARLVKLN   300
AETTRRRTEA ERKAAEEQAL QDAIKFTADF YKEVTEKFGA RTSEMARQLA EGARGKNIRS   360
SAEAIKSFEK HKDALNKKLS LKDRQAIAKA FDSLDKQMMA KSLEKFSKGF GVVGKAIDAA   420
SLYQEFKIST ETGDWKPFFV KIETLAAGAA ASWLVGIAFA TATATPIGIL GFALVMAVTG   480
AMIDEDLLEK ANNLVISI                                               498
```

```
SEQ ID NO: 14              moltype = AA  length = 300
FEATURE                    Location/Qualifiers
source                     1..300
                           mol_type = protein
                           organism = Pseudomonas aeruginosa
SEQUENCE: 14
MSNDNEVPGS MVIVAQGPDD QYAYEVPPID SAAVAGNMFG DLIQREIYLQ KNIYYPVRSI    60
FEQGTKEKKE INKKVSDQVD GLLKQITQGK REATRQERVD VMSAVLHKME SDLEGYKKTF   120
TKGPFIDYEK QSSLSIYEAW VKIWEKNSWE ERKKYPFQQL VRDELERAVA YYKQDSLSEA   180
VKVLRQELNK QKALKEKEDL SQLERDYRTR KANLEMKVQS ELDQAGSALP PLVSPTPEQW   240
LERATRLVTQ AIADKKQLQT TNNTLIKNSP TPLEKQKAIY NGELLVDEIA SLQARLVKLN   300

SEQ ID NO: 15              moltype = AA  length = 150
FEATURE                    Location/Qualifiers
source                     1..150
                           mol_type = protein
                           organism = Pseudomonas aeruginosa
SEQUENCE: 15
ERKKYPFQQL VRDELERAVA YYKQDSLSEA VKVLRQELNK QKALKEKEDL SQLERDYRTR    60
KANLEMKVQS ELDQAGSALP PLVSPTPEQW LERATRLVTQ AIADKKQLQT TNNTLIKNSP   120
TPLEKQKAIY NGELLVDEIA SLQARLVKLN                                   150

SEQ ID NO: 16              moltype = AA  length = 150
FEATURE                    Location/Qualifiers
source                     1..150
                           mol_type = protein
                           organism = Pseudomonas aeruginosa
SEQUENCE: 16
MSNDNEVPGS MVIVAQGPDD QYAYEVPPID SAAVAGNMFG DLIQREIYLQ KNIYYPVRSI    60
FEQGTKEKKE INKKVSDQVD GLLKQITQGK REATRQERVD VMSAVLHKME SDLEGYKKTF   120
TKGPFIDYEK QSSLSIYEAW VKIWEKNSWE                                   150

SEQ ID NO: 17              moltype = AA  length = 198
FEATURE                    Location/Qualifiers
source                     1..198
                           mol_type = protein
                           organism = Pseudomonas aeruginosa
SEQUENCE: 17
AETTRRRTEA ERKAAEEQAL QDAIKFTADF YKEVTEKFGA RTSEMARQLA EGARGKNIRS    60
SAEAIKSFEK HKDALNKKLS LKDRQAIAKA FDSLDKQMMA KSLEKFSKGF GVVGKAIDAA   120
SLYQEFKIST ETGDWKPFFV KIETLAAGAA ASWLVGIAFA TATATPIGIL GFALVMAVTG   180
AMIDEDLLEK ANNLVISI                                                198

SEQ ID NO: 18              moltype = AA  length = 777
FEATURE                    Location/Qualifiers
source                     1..777
                           mol_type = protein
                           organism = Pseudomonas aeruginosa
SEQUENCE: 18
MSDVFDLGSM TTVATATGQY SFYTPPPPTP IPYLTYIARP GINKFDLPEG AKIKDLIKRY    60
QYIGSQIPAA IMIRGVQEEI KKSTNTALAN VGAIVDGELA YLASQKKEKL NPAEATPLQM   120
ASAEKAAAVE LLASKQKELA DARTIANAFF GYDPLTVNYV NVMNEIYGRR EDKDFSFDNW   180
SKSYSAAQKI RLIEAKISVL NSRSSALDGK VAELTRLQRL EDAQHAAEAA RQTEAERLAQ   240
EQRQAEARRQ AEEARRQAEA QRQAELQRLA EAEAKRVAEA EKKRQDEINA RLQAIVVSES   300
EAKRIEEIYK RLEEQDKISN PTVTTPPAVD AGSRVDDALA HTGTRVTSGG ETGATGGSGR   360
DVDTGTGQGG ITARPVDVGS VSIPDRRDPK IPDQPRRDLG SLVPTFPDFP TFPSFPGVGV   420
PAAAKPLIPA GGGAASVSRT LKTAVDLLSV ARKTPGAMLG QVAAVVATMA VSSFWPKLNN   480
GERQASFAIP VAELSPPLAV DWQAIAAAKG TVDLPYRLKT LNVDGSIQII AVPTEPGSAA   540
VPVRALTLDS ASGTYKYTTT GPGGGTILVT PDTPPGQIDP SSSTPAVPRG PLIMPGTLLI   600
PKEPQIESYP ELDQREFNDG IYVYPEDSGI PPLYIVYRDP RDEPGVATGN GQPVTGNWLA   660
GASQGDGVPI PSQIADQLRG KEFKSWRDFR EQFWMAVSKD PSALENLSPS NRYFVSQGLA   720
PYAVPEEHLG SKEKFEIHHV VPLESGGALY NIDNLVIVTP KRHSEIHKEL KLKRKEK      777

SEQ ID NO: 19              moltype = AA  length = 639
FEATURE                    Location/Qualifiers
source                     1..639
                           mol_type = protein
                           organism = Pseudomonas aeruginosa
SEQUENCE: 19
MSDVFDLGSM TTVATATGQY SFYTPPPPTP IPYLTYIARP GINKFDLPEG AKIKDLIKRY    60
QYIGSQIPAA IMIRGVQEEI KKSTNTALAN VGAIVDGELA YLASQKKEKL NPAEATPLQM   120
ASAEKAAAVE LLASKQKELA DARTIANAFF GYDPLTVNYV NVMNEIYGRR EDKDFSFDNW   180
SKSYSAAQKI RLIEAKISVL NSRSSALDGK VAELTRLQRL EDAQHAAEAA RQTEAERLAQ   240
EQRQAEARRQ AEEARRQAEA QRQAELQRLA EAEAKRVAEA EKKRQDEINA RLQAIVVSES   300
EAKRIEEIYK RLEEQDKISN PTVTTPPAVD AGSRVDDALA HTGTRVTSGG ETGATGGSGR   360
DVDTGTGQGG ITARPVDVGS VSIPDRRDPK IPDQPRRDLG SLVPTFPDFP TFPSFPGVGV   420
PAAAKPLIPA GGGAASVSRT LKTAVDLLSV ARKTPGAMLG QVAAVVATMA VSSFWPKLNN   480
GERQASFAIP VAELSPPLAV DWQAIAAAKG TVDLPYRLKT LNVDGSIQII AVPTEPGSAA   540
```

```
VPVRALTLDS ASGTYKYTTT GPGGGTILVT PDTPPGQIDP SSSTPAVPRG PLIMPGTLLI    600
PKEPQIESYP ELDQREFNDG IYVYPEDSGI PPLYIVYRD                           639

SEQ ID NO: 20           moltype = AA   length = 239
FEATURE                 Location/Qualifiers
source                  1..239
                        mol_type = protein
                        organism = Pseudomonas aeruginosa
SEQUENCE: 20
MSDVFDLGSM TTVATATGQY SFYTPPPPTP IPYLTYIARP GINKFDLPEG AKIKDLIKRY    60
QYIGSQIPAA IMIRGVQEEI KKSTNTALAN VGAIVDGELA YLASQKKEKL NPAEATPLQM    120
ASAEKAAAVE LLASKQKELA DARTIANAFF GYDPLTVNYV NVMNEIYGRR EDKDFSFDNW    180
SKSYSAAQKI RLIEAKISVL NSRSSALDGK VAELTRLQRL EDAQHAAEAA RQTEAERLA     239

SEQ ID NO: 21           moltype = AA   length = 160
FEATURE                 Location/Qualifiers
source                  1..160
                        mol_type = protein
                        organism = Pseudomonas aeruginosa
SEQUENCE: 21
QEQRQAEARR QAEEARRQAE AQRQAELQRL AEAEAKRVAE AEKKRQDEIN ARLQAIVVSE    60
SEAKRIEEIY KRLEEQDKIS NPTVTTPPAV DAGSRVDDAL AHTGTRVTSG GETGATGGSG    120
RDVDTGTGQG GITARPVDVG SVSIPDRRDP KIPDQPRRDL                          160

SEQ ID NO: 22           moltype = AA   length = 240
FEATURE                 Location/Qualifiers
source                  1..240
                        mol_type = protein
                        organism = Pseudomonas aeruginosa
SEQUENCE: 22
GSLVPTFPDF PTFPSFPGVG VPAAAKPLIP AGGGAASVSR TLKTAVDLLS VARKTPGAML    60
GQVAAVVATM AVSSFWPKLN NGERQASFAI PVAELSPPLA VDWQAIAAAK GTVDLPYRLK    120
TLNVDGSIQI IAVPTEPGSA AVPVRALTLD SASGTYKYTT TGPGGGTILV TPDTPPGQID    180
PSSSTPAVPR GPLIMPGTLL IPKEPQIESY PELDQREFND GIYVYPEDSG IPPLYIVYRD    240

SEQ ID NO: 23           moltype = AA   length = 138
FEATURE                 Location/Qualifiers
source                  1..138
                        mol_type = protein
                        organism = Pseudomonas aeruginosa
SEQUENCE: 23
PRDEPGVATG NGQPVTGNWL AGASQGDGVP IPSQIADQLR GKEFKSWRDF REQFWMAVSK    60
DPSALENLSP SNRYFVSQGL APYAVPEEHL GSKEKFEIHH VVPLESGGAL YNIDNLVIVT    120
PKRHSEIHKE LKLRKEK                                                   138

SEQ ID NO: 24           moltype = AA   length = 256
FEATURE                 Location/Qualifiers
source                  1..256
                        mol_type = protein
                        organism = Pseudomonas aeruginosa
SEQUENCE: 24
MASSLAPRQV IRDGQFITSP NGKYKLVMQA DGNLVLYEDG TKPIWNTTPV GPGAKAVMEF    60
NLNLYNKAGQ VAWSSNVYTA YLFEEFKDEA YLNLQDDGDF GIFSDEAKWG SIVLSRPEVG    120
VKNKIIPTGT VMVPGTEYIN GNYRLAFQGD GNLVIYQINP QVVIWATYTM GADRAVVQED    180
GNFVIYKGTT ALWHTHTATG MPAYLKFTNT GKLFLSQPTL LWTLKRGSLS KPPKVIPGQH    240
GPLDTTPIWS WPHDYP                                                    256

SEQ ID NO: 25           moltype = AA   length = 87
FEATURE                 Location/Qualifiers
source                  1..87
                        mol_type = protein
                        organism = Pseudomonas aeruginosa
SEQUENCE: 25
MKSKISEYTE KEFLEFVKDI YTNNKKKFPT EESHIQAVLE FKKLTEHPSG SDLLYYPNEN    60
REDSPAGVVK EVKEWRASKG LPGFKAG                                        87

SEQ ID NO: 26           moltype = AA   length = 90
FEATURE                 Location/Qualifiers
source                  1..90
                        mol_type = protein
                        organism = Pseudomonas aeruginosa
SEQUENCE: 26
MSMEMIDIAK RLLASSIDGK TFSEEFFKTW RSERDSGVLA QDDASLGRCL SLMFGLADSF    60
TEGKKERPGE LTEGELKIAL SDLLKEYKYI                                     90

SEQ ID NO: 27           moltype = AA   length = 108
FEATURE                 Location/Qualifiers
source                  1..108
                        mol_type = protein
```

-continued

```
                           organism = Pseudomonas aeruginosa
SEQUENCE: 27
MSFKYYWAKF FWGAFFFVLV AWKGSVFPSL ASVNPLVVAG LSTILFPFSV KLVEDFALKY      60
TEREFWVTGF FSETPAKTGL YAVFYLSCYL FSIPLGMVFL FYKYGKAS                  108

SEQ ID NO: 28              moltype = AA   length = 90
FEATURE                    Location/Qualifiers
source                     1..90
                           mol_type = protein
                           organism = Pseudomonas aeruginosa
SEQUENCE: 28
MDIKNNLSDY TESEFLEIIE EFFKNKSGLK GSELEKRMDK LVKHFEEVTS HPRKSGVIFH      60
PKPGFETPEG IVKEVKEWRA ANGLPGFKAG                                      90

SEQ ID NO: 29              moltype = AA   length = 8
FEATURE                    Location/Qualifiers
source                     1..8
                           mol_type = protein
                           organism = synthetic construct
SEQUENCE: 29
QXDXNXVY                                                                8

SEQ ID NO: 30              moltype = AA   length = 8
FEATURE                    Location/Qualifiers
source                     1..8
                           mol_type = protein
                           organism = synthetic construct
SEQUENCE: 30
QXDXNXVF                                                                8

SEQ ID NO: 31              moltype = AA   length = 8
FEATURE                    Location/Qualifiers
source                     1..8
                           mol_type = protein
                           organism = synthetic construct
SEQUENCE: 31
QXDXNXGY                                                                8

SEQ ID NO: 32              moltype = AA   length = 8
FEATURE                    Location/Qualifiers
source                     1..8
                           mol_type = protein
                           organism = synthetic construct
SEQUENCE: 32
QXDXNXGF                                                                8

SEQ ID NO: 33              moltype = AA   length = 8
FEATURE                    Location/Qualifiers
source                     1..8
                           mol_type = protein
                           organism = synthetic construct
SEQUENCE: 33
QXDXDXVY                                                                8

SEQ ID NO: 34              moltype = AA   length = 8
FEATURE                    Location/Qualifiers
source                     1..8
                           mol_type = protein
                           organism = synthetic construct
SEQUENCE: 34
QXDXDXVF                                                                8

SEQ ID NO: 35              moltype = AA   length = 8
FEATURE                    Location/Qualifiers
source                     1..8
                           mol_type = protein
                           organism = synthetic construct
SEQUENCE: 35
QXDXDXGY                                                                8

SEQ ID NO: 36              moltype = AA   length = 8
FEATURE                    Location/Qualifiers
source                     1..8
                           mol_type = protein
                           organism = synthetic construct
SEQUENCE: 36
QXDXDXGF                                                                8

SEQ ID NO: 37              moltype = DNA  length = 32
```

-continued

```
FEATURE                 Location/Qualifiers
source                  1..32
                        mol_type = other DNA
                        organism = synthetic construct
SEQUENCE: 37
acagatcata tgagcgacgt ttttgacctt gg                                    32

SEQ ID NO: 38           moltype = DNA  length = 31
FEATURE                 Location/Qualifiers
source                  1..31
                        mol_type = other DNA
                        organism = synthetic construct
SEQUENCE: 38
acagatctcg aggccagcct tgaagccagg g                                     31

SEQ ID NO: 39           moltype = DNA  length = 29
FEATURE                 Location/Qualifiers
source                  1..29
                        mol_type = other DNA
                        organism = synthetic construct
SEQUENCE: 39
gagacatatg tccaatgaca acgaagtac                                        29

SEQ ID NO: 40           moltype = DNA  length = 41
FEATURE                 Location/Qualifiers
source                  1..41
                        mol_type = other DNA
                        organism = synthetic construct
SEQUENCE: 40
tttgacgtct cgagttaaat ggatattaca agattgtttg c                          41
```

PULMONARY ADMINISTRATION OF PYOCINS FOR TREATING BACTERIAL RESPIRATORY INFECTIONS

CROSS REFERENCE TO RELATED APPLICATIONS

This application is a continuation application of U.S. application Ser. No. 15/512,548, filed Mar. 18, 2017, which is the National Phase application of International Patent Application No. PCT/EP2015/071768, filed Sep. 22, 2015, which designated the United States and claims priority to GB Application 1416788.6 filed Sep. 23, 2014, each of which is hereby incorporated in its entirety including all tables, figures and claims. These applications are incorporated herein by reference, in their entirety.

SEQUENCE LISTING

The official copy of the Sequence Listing is submitted concurrently with the specification as an WIPO Standard ST.26 formatted XML file with file name "4553.006US2.xml", a creation date of Feb. 21, 2023, and a size of 43 kilobytes. This Sequence Listing filed via USPTO Patent Center is part of the specification and is incorporated in its entirety by reference herein.

FIELD OF THE INVENTION

The invention relates to the treatment of bacterial respiratory infections, and in particular to the use of the bacterially-originating antibiotics known as pyocins to treat such infections.

BACKGROUND TO THE INVENTION

For Gram-negative pathogens such as *Pseudomonas aeruginosa, Klebsiella pneumoniae* and *Escherichia coli* therapeutic options are often limited. This is due to the horizontal acquisition of antibiotic resistance determinants and the presence of a highly impermeable outer-membrane that severely limits the efficacy of many classes of antibiotics[1-3]. In the case of the opportunistic pathogen *P. aeruginosa*, clinical isolates with resistance to all available antibiotics are prevalent worldwide and between 18 and 25% of clinical isolates are multidrug resistant[1,4]. In addition, the ability of *P. aeruginosa* to form multidrug resistant biofilms during chronic infection and the appearance of antibiotic resistant phenotypic variants during prolonged antibiotic therapy can render this pathogen essentially untreatable with existing antibiotics[5-7]. Chronic infection of the lower respiratory tract with *P. aeruginosa* is the leading cause of mortality in patients with cystic fibrosis, who despite receiving intensive antibiotic therapy have a median predicted survival of 41.5 years (2011)[8]. In addition, infection with *P. aeruginosa* is a major and growing cause of nosocomial infections such as ventilator-associated pneumonia. *P. aeruginosa* infection is also linked with the pathogenesis of chronic obstructive pulmonary disease, a leading cause of death in the Western world[9-12]. Consequently, there is an urgent need to consider alternative strategies for antibiotic development, to bolster a developmental pipeline that in recent decades has yielded few novel small molecule antibiotics active against these difficult to treat bacteria[13-15].

An alternative strategy for the discovery of effective antibiotics is to exploit the potent narrow-spectrum antibiotics produced by many bacteria for intraspecies competition. In *P. aeruginosa, K. pneumoniae* and *E. coli* these take the form of multi-domain protein antibiotics known as the S-type pyocins, klebicins and colicins respectively[16-18]. These bacteriocins have evolved to efficiently cross the Gram-negative outer membrane through the parasitisation of existing active nutrient uptake pathways, which are an Achilles' heel for Gram-negative bacteria[19-24]. The cellular targets of these protein antibiotics are highly conserved, with cytotoxic activity most commonly taking the form of a nuclease activity targeting DNA, rRNA or tRNA, or a pore-forming activity targeting the cytoplasmic membrane[17]. For the pyocins that have been characterized to date it is known that pyocins S1, S2, S3 and AP41 display DNase activity, pyocin S4 is a tRNase and pyocin S5 is a pore-forming toxin[16]. For the recently described lectin-like pyocin L1 the mechanism of cell killing is unknown.

SUMMARY OF THE INVENTION

Although pyocins display unmatched potency against *P. aeruginosa*, and pyocin S2 is active in an invertebrate model of *P. aeruginosa* infection[25], pyocins have not previously been suggested or shown to be good candidates for clinical use. As bacterially-derived polypeptides, they would appear particularly unsuitable for use in treating conditions affecting the respiratory tract, since the presence of bacterial proteins in the lung would be expected to provoke an immune response which could be very damaging to the sensitive respiratory tissue.

Surprisingly, the present inventors have found that S-type pyocins can be successfully delivered to the lung, providing a dramatic reduction in bacterial load, but without provoking an immune response or causing other tissue damage.

The invention provides an S-type pyocin for use in a method of prophylaxis or treatment of a bacterial respiratory infection, wherein the pyocin is delivered by pulmonary administration.

The invention further provides the use of an S-type pyocin in the manufacture of a medicament for the prophylaxis or treatment of a bacterial respiratory infection, wherein the pyocin is delivered by pulmonary administration.

The invention further provides a method for prophylaxis or treatment of bacterial respiratory infection in a subject wherein an S-type pyocin is delivered to the subject by pulmonary administration.

The infecting bacteria typically comprise *Pseudomonas* species, such as *Pseudomonas aeruginosa*.

The subject to be treated may have, or may be at risk of developing a bacterial pneumonia as a result of the infection. Thus the S-type pyocins may be used for the prophylaxis and/or treatment of bacterial pneumonia.

The subject to be treated may have compromised respiratory tract function and/or compromised immune function.

The subject to be treated may be suffering from cystic fibrosis or chronic obstructive pulmonary disease (COPD). Alternatively, the subject may be a cancer patient (especially one undergoing chemotherapy), or a patient affected by congestive heart failure or AIDS.

The subject to be treated may have, or be at risk of developing, community-acquired pneumonia and nosocomial infections such as ventilator-associated pneumonia and hospital-acquired pneumonia.

As described in more detail below, S-type pyocins comprise a targeting portion and an effector portion.

The S-type pyocin may, for example, comprise an S2, SD2, S5 or AP41 targeting portion. In some embodiments, the pyocin comprises an S5 targeting portion.

Additionally or alternatively, the S-type pyocin may, for example, comprise an S2, SD2, S5 or AP41 effector portion. Alternatively it may comprise a cytotoxic domain from a colicin, e.g. from an E2 or E3 colicin. In some embodiments, the pyocin comprises an S5 effector portion.

In some embodiments, the S-type pyocin is an SD2, SD2, S5, AP41 or L1 pyocin, e.g. an S5 pyocin.

It may be desirable that a combination of two or more pyocins is administered to the subject. The combination may comprise S-type pyocins having at least two different receptor specificities and/or effector activities.

The combination may comprise an S5 pyocin.
The combination may comprise an L1 pyocin.
The combination may comprise an S2 pyocin.
The combination may comprise an AP41 pyocin.
The combination may comprise an SD2 pyocin.

The combination may comprise an L1 pyocin and an S2 pyocin; an L1 pyocin and an AP41 pyocin; an S2 pyocin and an AP41 pyocin; or an L1 pyocin, an S2 pyocin and an AP41 pyocin. Any of these combinations may additionally comprise an S5 pyocin and/or an SD2 pyocin. Whichever other pyocins are present, it may be desirable that the combination comprises an S5 pyocin.

The invention further provides a method of preparing a medicament for the prophylaxis or treatment of bacterial respiratory infection comprising providing an S-type pyocin and formulating said S-type pyocin for pulmonary administration.

The S-type pyocin may have been expressed by recombinant methods.

The method may comprise the steps of recombinantly expressing the S-type pyocin and optionally isolating the S-type pyocin.

The invention further provides a device for pulmonary administration of an active agent to a subject, the device comprising an S-type pyocin. The device may, for example, be an inhaler (e.g. metered-dose inhaler, dry powder inhaler) or nebuliser (e.g. ultrasonic nebuliser, jet nebuliser, vibrating mesh nebuliser).

The invention will now be described in more detail, by way of example and not limitation, by reference to the accompanying drawings and examples.

DETAILED DESCRIPTION OF THE INVENTION

Pyocins

Figure 1:
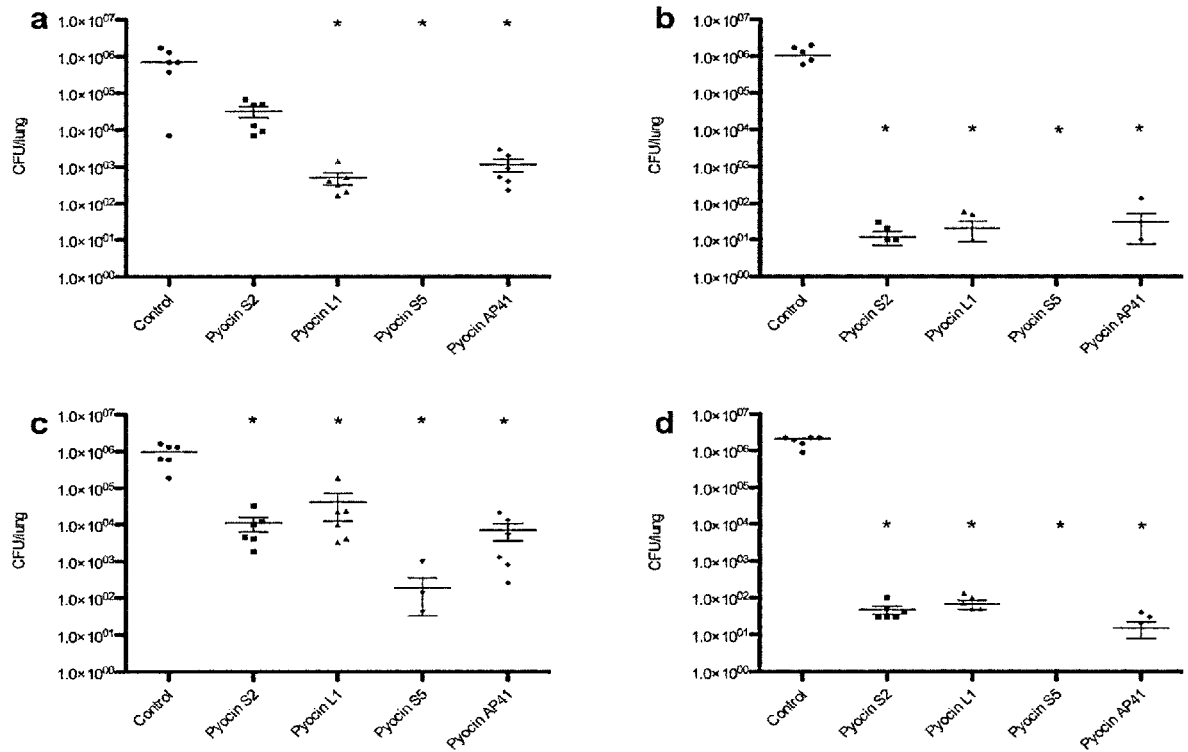
FIG. 1. *P. aeruginosa* P8 bacterial recovery from pyocin treated mice. All pyocins were given at 3 mg ml$^{-1}$. Bacterial counts determined by CFU counts of homogenized lungs. (a) Mice treated with pyocin 6 h pre-infection, all mice culled 5 h post-infection (b) Mice treated with pyocin 6 h pre-infection, pyocin treated mice survived to 24 h (c) Mice treated with pyocin 1 h post-infection, all mice culled 4.5 h post-infection (d) Mice treated with pyocin 1 h post-infection, pyocin treated mice survived to 24 h. No colonies were recovered from pyocin S5 treated mice in a) b) and d). Bars represent Mean±SEM, * denotes statistical significance for comparison of treatment versus control by a one-sided Mann-Whitney U test with Bonferroni correction applied.

Pyocins are proteinaceous anti-microbial toxins produced by and effective against *Pseudomonas* species, especially *P. aeruginosa*.

Pyocins generally fall into three classes, namely S-type, R-type and F-type.

R-type (rod-like) and F-type (flexible and non-contractile) pyocins are both related to phage tail proteins (from P2 phage and lambda phage respectively) and act by forming pores in the bacterial membrane.

S-type (soluble) pyocins have characteristic multi-domain structures similar to colicins (to which they are believed to be evolutionarily related). The term "pyocin" is used in this specification to refer to S-type pyocins except where the context demands otherwise. Organisms which produce S-type pyocins are normally unaffected by their own pyocins because they also produce "immunity proteins" which act as antagonists to the corresponding pyocins.

S-type pyocins comprise a targeting portion and an effector portion. Typically the targeting portion is at the N-terminal end of the molecule and the effector portion at the C-terminal end. However, the order of these portions may not be essential for function. Thus use of pyocin molecules having an N-terminal effector portion and a C-terminal targeting portion is also contemplated.

The effector portion may constitute a single independently folded domain. The targeting portion may also constitute a single independently folded domain or may be sub-divided into two or more independently folded domains.

The targeting portion binds to a receptor at the surface of the target organism (i.e. at the Gram negative outer membrane) and mediates translocation of the pyocin across the outer membrane. For the avoidance of doubt, the term "receptor" is used simply to designate the molecule on the target organism to which the targeting portion binds, and should not be taken to imply a cooperative receptor-ligand interaction in the sense usually intended for a pair of molecules expressed by a single organism.

In general, the targeting portion of the pyocin determines the species and strain specificity (or tropism) of the pyocin. The receptors to which they bind are often specific to pseudomonads, e.g. to *Pseudomonas*, or even to *P. aeruginosa* or strains thereof.

The targeting portions of most naturally occurring S-type pyocins have a characteristic modular structure containing up to three identifiable sub-regions, each of which may represent an separately folded domain or may lack recognisable secondary structure and thus form a flexible region of the molecule. These sub-regions are often referred to in the literature as a receptor binding region, a region of unknown function, and a translocation region, and typically (although not exclusively) occur in that order in an N- to C-terminal direction. However, these proteins are not well characterised and the ascribed functions may not be correct. These regions will therefore be referred to herein as regions I, II and III of the targeting portion respectively.

Without wishing to be bound by any particular theory, it is believed that regions I, II and III may be interchangeable between pyocin molecules, at least to some extent, and that region II may be dispensable in whole or in part. Thus, the targeting portion may comprise at least a region I sequence and a region III sequence, optionally separated by a region II sequence, a fragment thereof, or a peptide linker. It may be desirable that region I, region II or fragment or linker (if present), and region III occur in that order in an N- to C-terminal direction.

The effector portion typically has cell-killing activity once across the outer membrane. It may act in the periplasm or may require transport to the cytoplasm to exert its cell-killing effect. Regardless of mechanism, the effector portion may be referred to as a "cytotoxic" portion of the pyocin molecule.

The effector or cytotoxic portions of pyocin molecules are typically pore-forming or enzymatic. Pore-forming pyocins, e.g. pyocin S5, kill target cells by depolarisation of the cytoplasmic membrane. Enzymatic pyocins typically act as nucleases in the cytoplasm and include those with DNase activity (e.g. pyocins S1, S2, SD2, S3 and AP41) and tRNase activity (e.g. pyocin S4).

The targets on which the effector portions act tend to be highly conserved across the bacterial kingdom and their mechanisms of action are similar to those of other anti-bacterial toxins such as the effector domains of colicins. Indeed, chimeric pyocins containing a targeting portion from an S1 or S2 pyocin linked to an effector portion from either an E2 or E3 colicin have been demonstrated to retain pseudomonad-killing activity[37]. Thus the pyocin may comprise any suitable anti-bacterial protein or protein domain as an effector portion, as long as the protein or domain retains cytotoxic activity against one or more pseudomonad organisms. For example, the effector component may be a cytotoxic domain from a colicin, such as (but not limited to) an E2 or E3 colicin.

Pyocin S2

The targeting domains of S2 pyocins bind to the TonB-dependent iron-siderophore receptor FpvAI. S2 effector domains have DNase activity.

An example of an S2 pyocin has the sequence:

[SEQ ID NO: 1]
MAVNDYEPGSMVITHVQGGGRDIIQYIPARSSYGIPPFVPPGPSPYVGIG

MQEYRKLRSILDKSHSELKKNLKNETLKEVDELKSEAGLPGKAVSANDIR

DEKSIVDALMDAKAKSLKAIEDRPANLYTASDFPQKSESMYQSQLLASRK

FYGEFLDRHMSELAKAYSADIYKAQIAILKQTSQELENKARSLEAEAQRA

AAEVEADYKARKANVEKKVQSELDQAGNALPQLTNPIPEQWLERATQLVT

QAIANKKKLQTANNALIAKAPNALEKQKATYNADLLVDEIASLQARLDKL

NAETARRKEIARQAAIRAANTYAMPANGSVVATAAGRGLIQVAQGAASLA

QAISDAIAVLGRVLASAPSVMAVGFASLTYSSRTAEQWQDQTPDSVRYAL

GMDAAKLGLPPSVNLNAVAKASGTVDLPMRLTNEARGNITTLSVVSIDGV

SVPKAVPVRMAAYNATTGLYEVTVPSTTAEAPPLILTWTPASPPGNQNPS

SITPVVPKPVPVYEGATLIPVKATPETYPGVITLPEDLIIGFPADSGIKP

IYVMFRDPRDVPGAATGKGQPVSGNWLGAASQGEGAPIPSQIADKLRGKI

FKNWRDFREQFWIAVANDPELSKQFNPGSLAVMRDGGAPYVRESEQAGGR

IKIEIHHKVRIADGGGVYNMGNLVAVTPKRHIEIHKGGK

The targeting portion of the S2 pyocin has the sequence:

[SEQ ID NO: 2]
MAVNDYEPGSMVITHVQGGGRDIIQYIPARSSYGTPPFVPPGPSPYVGTG

MQEYRKLRSTLDKSHSELKKNLKNETLKEVDELKSEAGLPGKAVSANDIR

DEKSIVDALMDAKAKSLKAIEDRPANLYTASDEPQKSESMYQSQLLASRK

FYGEFLDRHMSELAKAYSADIYKAQIAILKQTSQELENKARSLEAEAQRA

AAEVEADYKARKANVEKKVQSELDQAGNALPQLTNPTPEQWLERATQLVT

QATANKKKLQTANNALIAKAPNALEKQKATYNADLLVDEIASLQARLDKL

NAETARRKEIARQAAIRAANTYAMPANGSVVATAAGRGLIQVAQGAASLA

QAISDAIAVLGRVLASAPSVMAVGFASLTYSSRTAEQWQDQTPDSVRYAL

GMDAAKLGLPPSVNLNAVAKASGTVDLPMRLTNEARGNTTTLSVVSTDGV

SVPKAVPVRMAAYNATTGLYEVTVPSTTAEAPPLILTWTPASPPGNQNPS

STTPVVPKPVPVYEGATLTPVKATPETYPGVITLPEDLIIGFPADSGIKP

IYVMFRDP

Region I of the S2 targeting portion has the sequence:

[SEQ ID NO: 3]
MAVNDYEPGSMVITHVQGGGRDIIQYIPARSSYGTPPFVPPGPSPYVGTG

MQEYRKLRSTLDKSHSELKKNLKNETLKEVDELKSEAGLPGKAVSANDIR

DEKSIVDALMDAKAKSLKAIEDRPANLYTASDFPQKSESMYQSQLLASRK

FYGEFLDRHMSELAKAYSADIYKAQIAILKQTSQELENKARSLEAEAQRA

AAEVEADYKARKANVE

Region II of the S2 targeting portion has the sequence:

[SEQ ID NO: 4]
KKVQSELDQAGNALPQLTNPTPEQWLERATQLVTQATANKKKLQTANNAL

IAKAPNALEKQKATYNADLLVDEIASLQARLDKLNAETARRKEIAR

Region III of the S2 targeting portion has the sequence:

[SEQ ID NO: 5]
AAIRAANTYAMPANGSVVATAAGRGLIQVAQGAASLAQATSDAIAVLGRV

LASAPSVMAVGFASLTYSSRTAEQWQDQTPDSVRYALGMDAAKLGLPPSV

NLNAVAKASGTVDLPMRLTNEARGNTTTLSVVSTDGVSVPKAVPVRMAAY

NATTGLYEVIVPSTTAEAPPLILTWTPASPPGNQNPSSTTPVVPKPVPVY

EGATLTPVKATPETYPGVITLPEDLIIGFPADSGIKPIYVMFRDP

The effector portion of the S2 pyocin has the sequence:

[SEQ ID NO: 6]
RDVPGAATGKGQPVSGNWLGAASQGEGAPIPSQIADKLRGKTFKNWRDFR

EQFWIAVANDPELSKQFNPGSLAVMRDGGAPYVRESEQAGGRIKIEIHHK

VRIADGGGVYNMGNLVAVTPKRHIEIHKGGK

Pyocin SD2

A prototypical SD2 pyocin sequence is described by McCaughey et al. (in press). The targeting domains of SD2 pyocins bind to lipopolysaccharide (LPS) from *P. aeruginosa* and more specifically to the common polysaccharide antigen (CPA) within LPS, which is predominantly a homopolymer of D-rhamnose. although specific binding may not be required for killing. SD2 effector domains are believed to have tRNase activity.

An example of an SD2 pyocin has the sequence:

[SEQ ID NO: 7]
MAVNDYEPGSMVITHVQGGGRDIIQYIPARSSYGTPPFVPPGPSPYVGTG

MQEYRKLRSTLDKSHSELKKNLKNETLKEVDELKSEAGLPGKAVSANDIR

DEKSIVDALMDAKAKSLKAIEDRPANLYTASDFPQKSESMYQSQLLASRK

FYGEFLDRHMSELAKAYSADIYKAQIAILKQTSQELENKARSLEAEAQRA

AAEVEADYKARKANVEKKVQSELDQAGNALPQLTNPTPEQWLERATQLVT

QAIANKKKLQTANNALIAKAPNALEKQKATYNADLLVDEIASLQARLDKL

NAETARRKEIARQAAIRAANTYAMPANGSVVATAAGRGLIQVAQGAASLA

QAISDAIAVLGRVLASAPSVMAVGFASLTYSSRTAEQWQDQTPDSVRYAL

GMDANKLGLTSSVNLSAVAKAGGTVDLPMRLTNEARGNTTTLSVVSTDGV

SVPKAAPVRMAAYNATTGLYEVTVPSTTAEAPPLILTWTPASPPGNQNPS

STTPVIPKPVPVYEGAALTPLKTGPESYPGMLLDLNDLIVIFPADSGVKP

VYVMLSSPLDSGIFTRRQLQKKEDSHKYDEGLGEKSANNGTLAEFRDKIL

EHLADPATVEKGTYHSEVNSKVHYNARTNIVVIIGEDGMFVSGWRIEPGT

DQYNFYMKNEVL

The targeting portion of the SD2 pyocin has the sequence:

[SEQ ID NO: 8]
MAVNDYEPGSMVITHVQGGGRDIIQYIPARSSYGTPPFVPPGPSPYVGTG

MQEYRKLRSTLDKSHSELKKNLKNETLKEVDELKSEAGLPGKAVSANDIR

DEKSIVDALMDAKAKSLKAIEDRPANLYTASDFPQKSESMYQSQLLASRK

FYGEFLDRHMSELAKAYSADIYKAQIAILKQTSQELENKARSLEAEAQRA

AAEVEADYKARKANVEKKVQSELDQAGNALPQLTNPTPEQWLERATQLVT

QAIANKKKLQTANNALIAKAPNALEKQKATYNADLLVDEIASLQARLDKL

NAETARRKEIARQAAIRAANTYAMPANGSVVATAAGRGLIQVAQGAASLA

QAISDAIAVLGRVLASAPSVMAVGFASLTYSSRTAEQWQDQTPDSVRYAL

GMDANKLGLTSSVNLSAVAKAGGTVDLPMRLTNEARGNTTTLSVVSTDGV

SVPKAAPVRMAAYNATTGLYEVTVPSTTAEAPPLILTWTPASPPGNQNPS

STTPVIPKPVPVYEGAALTPLKTGPESYPGMLLDLNDLIVIFPADSGVKP

VYVM

Region I of the SD2 targeting portion has the sequence:

[SEQ ID NO: 9]
MAVNDYEPGSMVITHVQGGGRDIIQYIPARSSYGTPPFVPPGPSPYVGTG

MQEYRKLRSTLDKSHSELKKNLKNETLKEVDELKSEAGLPGKAVSANDIR

DEKSIVDALMDAKAKSLKAIEDRPANLYTASDFPQKSESMYQSQLLASRK

FYGEFLDRHMSELAKAYSADIYKAQIAILKQTSQELENKARSLEAEAQRA

AAEVEADYKARKANVE

Region II of said pyocin SD2 targeting portion:

[SEQ ID NO: 10]
KKVQSELDQAGNALPQLTNPTPEQWLERATQLVTQAIANKKKLQTANNAL

IAKAPNALEKQKATYNADLLVDEIASLQARLDKLNAETARRKEIAR

Region III of the SD2 targeting portion has the sequence:

[SEQ ID NO: 11]
QAAIRAANTYAMPANGSVVATAAGRGLIQVAQGAASLAQAISDAIAVLGR

VLASAPSVMAVGFASLTYSSRTAEQWQDQTPDSVRYALGMDANKLGLTSS

VNLSAVAKAGGTVDLPMRLTNEARGNTTTLSVVSTDGVSVPKAAPVRMAA

YNATTGLYEVTVPSTTAEAPPLILTWTPASPPGNQNPSSTTPVIPKPVPV

YEGAALTPLKTGPESYPGMLLDLNDLIVIFPADSGVKPVYVM

The effector portion of SD2 pyocin has the sequence:

[SEQ ID NO: 12]
LSSPLDSGIFTRRQLQKKFDSHKYDFGLGEKSANNGTLAEFRDKILEHLA

DPATVEKGTYHSEVNSKVHYNARTNIVVIIGEDGMFVSGWRIEPGTDQYN

FYMKNEVL

Pyocin S5

The targeting domains of S5 pyocins bind to the TonB-dependent iron-siderophore receptor FptA. S5 effector domains have pore-forming activity.

Sequence analysis of the targeting portion of pyocin S5 suggests that region III may occur N-terminal of region I, and that region II may be absent.

An example of an S5 pyocin has the sequence:

[SEQ ID NO: 13]
MSNDNEVPGSMVIVAQGPDDQYAYEVPPIDSAAVAGNMFGDLIQRETYLQ

KNIYYPVRSIFEQGTKEKKEINKKVSDQVDGLLKQITQGKREATRQERVD

VMSAVLHKMESDLEGYKKTFTKGPFIDYEKQSSLSIYEAWVKIWEKNSWE

ERKKYPFQQLVRDELERAVAYYKQDSLSEAVKVIRQELNKQKALKEKEDL

SQLERDYRTRKANLEMKVQSELDQAGSALPPLVSPTPEQWLERATRLVTQ

ATADKKQLQTTNNTLIKNSPTPLEKQKAIYNGELLVDEIASLQARLVKLN

AETTRRRTEAERKAAEEQALQDAIKFTADFYKEVTEKFGARTSEMARQLA

EGARGKNIRSSAEAIKSFEKHKDALNKKLSLKDRQATAKAFDSLDKQMMA

KSLEKESKGEGVVGKAIDAASLYQEFKISTETGDWHPFFVKIETLAAGAA

ASWLVGIAFATATATPIGILGFALVMAVTGAMIDEDLLEKANNLVISI

The targeting portion of the S5 pyocin has the sequence:

[SEQ ID NO: 14]
MSNDNEVPGSMVIVAQGPDDQYAYEVPPIDSAAVAGNMFGDLIQREIYLQ

KNIYYPVRSIFEQGTKEKKEINKKVSDQVDGLLKQITQGKREATRQERVD

VMSAVLHKMESDLEGYKKTFTKGPFIDYEKQSSLSIYEAWVKIWEKNSWE

ERKKYPFQQLVRDELERAVAYYKQDSLSEAVKVLRQELNKQKALKEKEDL

SQLERDYRTRKANLEMKVQSELDQAGSALPPLVSPTPEQWLERATRLVTQ

AIADKKQLQTTNNTLIKNSPTPLEKQKAIYNGELLVDEIASLQARLVKLN

Region I of the S5 targeting portion has the sequence:

[SEQ ID NO: 15]
ERKKYPFQQLVRDELERAVAYYKQDSLSEAVKVLRQELNKQKALKEKEDL

SQLERDYRTRKANLEMKVQSELDQAGSALPPLVSPTPEQWLERATRLVTQ

AIADKKQLQTTNNTLIKNSPTPLEKQKAIYNGELLVDEIASLQARLVKLN

Region III of the S5 targeting portion has the sequence:

[SEQ ID NO: 16]
MSNDNEVPGSMVIVAQGPDDQYAYEVPPIDSAAVAGNMFGDLIQRETYLQ

KNIYYPVRSIFEQGTKEKKEINKKVSDQVDGLLKQITQGKREATRQERVD

VMSAVLHKMESDLEGYKKIFTKGPFIDYEKQSSLSIYEAWVKIWEKNSWE

The effector portion of the S5 pyocin has the sequence:

[SEQ ID NO: 17]
AETTRRRTEAERKAAEEQALQDAIKFTADFYKEVTEKFGARTSEMARQLA

EGARGKNIRSSAEAIKSFEKHKDALNKKLSLKDRQATAKAFDSLDKQMMA

KSLEKFSKGFGVVGKAIDAASLYQEFKISTETGDWKPFFVKIETLAAGAA

ASWLVGIAFATATATPIGILGFALVMAVTGAMIDEDLLEKANNLVISI

Pyocin AP41

The effector domains of AP41 pyocins have DNase activity.

An example of an AP41 pyocin has the sequence:

[SEQ ID NO: 18]
MSDVFDLGSMTTVATATGQYSFYTPPPPTPIPYLTYIARPGINKFDLPEG

AKIKDLIKRYQYIGSQIPAAIMIRGVQEEIKKSTNTALANVGAIVDGELA

YLASQKKEKLNPAEATPLQMASAEKAAAVELLASKQKELADARTIANAFF

GYDPLTVNYVNVMNEIYGRREDKDFSEDNWSKSYSAAQKIRLIEAKISVL

NSRSSALDGKVAELTRLQRLEDAQHAAEAARQTEAERLAQEQRQAEARRQ

AEEARRQAEAQRQAELQRLAEAEAKRVAEAEKKRQDEINARLQAIVVSES

EAKRIEEIYKRLEEQDKISNPTVTTPPAVDAGSRVDDALAHTGTRVTSGG

ETGATGGSGRDVDTGTGQGGITARPVDVGSVSIPDRRDPKIPDQPRRDLG

SLVPTFPDEPTEPSFPGVGVPAAAKPLIPAGGGAASVSRTLKTAVDLLSV

ARKTPGAMLGQVAAVVATMAVSSFWPKLNNGERQASFAIPVAELSPPLAV

DWQAIAAAKGTVDLPYRLKTLNVDGSIQIIAVPTEPGSAAVPVRALTLDS

ASGTYKYTTTGPGGGTILVTPDTPPGQIDPSSSTPAVPRGPLIMPGTLLI

PKEPQIESYPELDQREFNDGIYVYPEDSGIPPLYIVYRDPRDEPGVATGN

GQPVTGNWLAGASQGDGVPIPSQIADQLRGKEFKSWRDFREQFWMAVSKD

PSALENLSPSNRYFVSQGLAPYAVPEEHLGSKEKFEIHHVVPLESGGALY

NIDNLVIVTPKRHSEIHKELKLKRKEK

The targeting portion of the AP41 pyocin has the sequence:

[SEQ ID NO: 19]
MSDVFDLGSMTTVATATGQYSFYTPPPPTPIPYLTYIARPGINKFDLPEG

AKIKDLIKRYQYIGSQIPAAIMIRGVQEEIKKSTNTALANVGAIVDGELA

-continued

YLASQKKEKLNPAEATPLQMASAEKAAAVELLASKQKELADARTIANAFF

GYDPLTVNYVNVMNEIYGRREDKDFSEDNWSKSYSAAQKIRLIEAKISVL

NSRSSALDGKVAELTRLQRLEDAQHAAEAARQTEAERLAQEQRQAEARRQ

AEEARRQAEAQRQAELQRLAEAEAKRVAEAEKKRQDEINARLQAIVVSES

EAKRIEETYKRLEEQDKISNPTVTTPPAVDAGSRVDDALAHTGTRVTSGG

ETGATGGSGRDVDTGTGQGGITARPVDVGSVSIPDRRDPKIPDQPRRDLG

SLVPTFPDFPTFPSFPGVGVPAAAKPLIPAGGGAASVSRTLKTAVDLLSV

ARKTPGAMLGQVAAVVATMAVSSFWPKLNNGERQASFAIPVAELSPPLAV

DWQATAAAKGTVDLPYRLKTLNVDGSIQIIAVPTEPGSAAVPVRALTLDS

ASGTYKYTTTGPGGGTILVTPDTPPGQIDPSSSTPAVPRGPLIMPGTLLI

PKEPQIESYPELDQREFNDGIYVYPEDSGIPPLYIVYRD

Region I of the AP41 targeting portion has the sequence:

[SEQ ID NO: 20]

MSDVFDLGSMTTVATATGQYSFYTPPPPTPIPYLTYIARPGINKFDLPEG

AKIKDLIKRYQYIGSQIPAAIMIRGVQEEIKKSTNTALANVGAIVDGELA

YLASQKKEKLNPAEATPLQMASAEKAAAVELLASKQKELADARTIANAFF

GYDPLTVNYVNVMNEIYGRREDKDFSEDNWSKSYSAAQKIRLIEAKISVL

NSRSSALDGKVAELTRLQRLEDAQHAAEAARQTEAERLA

Region II of the AP41 targeting portion has the sequence:

[SEQ ID NO: 21]

QEQRQAEARRQAEEARRQAEAQRQAELQRLAEAEAKRVAEAEKKRQDEIN

ARLQAIVVSESEAKRIEEIYKRLEEQDKISNPTVTTPPAVDAGSRVDDAL

AHTGTRVTSGGETGATGGSGRDVDTGTGQGGITARPVDVGSVSIPDRRDP

KIPDQPRRDL

Region III of the AP41 targeting portion has the sequence:

[SEQ ID NO: 22]

GSLVPTFPDEPTFPSFPGVGVPAAAKPLIPAGGGAASVSRTLKTAVDLLS

VARKTPGAMLGQVAAVVATMAVSSFWPKLNNGERQASFAIPVAELSPPLA

VDWQAIAAAKGTVDLPYRLKTLNVDGSIQIIAVPTEPGSAAVPVRALTLD

SASGTYKYTTTGPGGGTILVTPDTPPGQIDPSSSTPAVPRGPLIMPGTLL

IPKEPQIESYPELDQREENDGIYVYPEDSGIPPLYIVYRD

The effector portion of the AP41 pyocin has the sequence:

[SEQ ID NO: 23]

PRDEPGVATGNGQPVTGNWLAGASQGDGVPIPSQIADQLRGKEFKSWRDF

REQFWMAVSKDPSALENLSPSNRYFVSQGLAPYAVPEEHLGSKEKFEIHH

VVPLESGGALYNIDNLVIVTPKRHSEIHKELKLKRKEK

Pyocin L1

Pyocin L1 can be regarded as a "lectin-like" pyocin, which binds to carbohydrate moieties on the bacterial surface. Its receptor on *P. aeruginosa* is believed to be LPS, and more specifically the common polysaccharide antigen (CPA) within LPS, which is predominantly a homo-polymer of D-rhamnose.

For the purpose of this specification, it is regarded as an S-type pyocin because it is soluble and has no homology to phage tail proteins (and thus is not readily classifiable with R-type or F-type pyocins).

An example of an L1 pyocin has the sequence:

[SEQ ID NO: 24]

MASSLAPRQVIRDGQFITSPNGKYKLVMQADGNLVLYEDGTKPIWNTTPV

GPGAKAVMEENLNLYNKAGQVAWSSNVYTAYLFEEFKDEAYLNLQDDGDF

GIFSDEAKWGSIVLSRPEVGVKNKIIPTGTVMVPGTEYINGNYRLAFQGD

GNLVIYQINPQVVIWATYTMGADRAVVQEDGNFVIYKGTTALWHTHTATG

MPAYLKFTNTGKLFLSQPTLLWTLKRGSLSKPPKVIPGQHGPLDTTPIWS

WPHDYP

The four underlined sequences are believed to represent carbohydrate-binding motifs. An L1 pyocin typically comprises one, two, three or four carbohydrate-binding motifs having the consensus sequence Q-X-D-X-N/D-X-V/G-Y/F.

Thus, the S-type pyocin for use in the present invention comprises a targeting portion which may comprise:

- a region I sequence having at least 80% sequence identity, e.g. at least 85%, 90%, 95%, 96%, 97%, 98% or 99% sequence identity, to the region I sequence from pyocin S2, SD2, S5 or AP41 (SEQ ID NOs: 3, 9, 15 and 20 respectively);
- a region III sequence having at least 80% sequence identity, e.g. at least 85%, 90%, 95%, 96%, 97%, 98% or 99% sequence identity, to the region III sequence from pyocin S2, SD2, S5 or AP41 (SEQ ID NOs: 5, 11, 16 and 22 respectively);

and optionally:

- a region II sequence having at least 80% sequence identity, e.g. at least 85%, 90%, 95%, 96%, 97%, 98% or 99% sequence identity, to the region II sequence from pyocin S2, SD2 or AP41 (SEQ ID NOs: 4, 10 and 21 respectively).

The targeting portion may have at least 80% sequence identity, e.g. at least 85%, 90%, 95%, 96%, 97%, 98% or 99% sequence identity to the targeting portion sequence from pyocin S2, SD2, S5 or AP41 (SEQ ID NOs: 2, 8, 14 and 19 respectively). Such targeting portions may be described as S2, SD2, S5 and AP41 targeting portions respectively. Typically they will bind to the same receptor as the exemplary sequences provided here.

The S-type pyocin for use in the present invention comprises an effector portion which may have at least 80% sequence identity, e.g. at least 85%, 90%, 95%, 96%, 97%, 98% or 99% sequence identity to the effector region sequence from pyocin S2, SD2, S5 or AP41 (SEQ ID NOs: 6, 12, 17 and 23 respectively). Such effector portions may be described as S2, SD2, S5 and AP41 effector portions respectively. Typically, they have the same cytotoxic activity as the exemplary sequences provided, i.e. DNase (S2, SD2, AP41) or pore-forming (S5).

Alternatively the effector portion may be a cytotoxic domain from a colicin (e.g. a cytotoxic domain from colicin E1, E3, E9, D, Ia, E2, E7, E8, E4, E6, E5, A, B, N, M or S4.

Exemplary sequences are provided in WO2014/009744) or any other suitable cytotoxic protein.

The pyocin molecule may have at least 80% sequence identity, e.g. at least 85%, 90%, 95%, 96%, 97%, 98% or 99% sequence identity to the exemplary sequences of pyocin S2, SD2, S5, AP41 or L1 provided above (SEQ ID NOs: 1, 7, 13, 18 and 24 respectively). Such molecules may be described as SD2, SD2, S5, AP41 or L1 pyocins respectively. Typically, they bind to the same receptors and have the same cytotoxic activity as the exemplary sequences provided. An L1 pyocin typically comprises one, two, three or four carbohydrate binding motifs which each conform to the consensus sequence shown above. An In some embodiments, an L1 pyocin comprises one, two, three or all four of the specific carbohydrate binding motifs underlined in SEQ ID NO: 24 above.

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Pyocin proteins may be synthesised or purified by any appropriate method. For example, they may be purified from organisms (*Pseudomonas* sp.) which naturally express them, they may be synthesised by chemical methods, they may be expressed in cell-free systems, or they may be expressed by non-*Pseudomonas* host cells comprising nucleic acid encoding the relevant pyocin.

The host cell may be prokaryotic or eukaryotic, although prokaryotic hosts may be preferred since the pyocins are themselves bacterial proteins. Prokaryotic hosts may be gram-positive or gram-negative. *E. coli* is an example of a common gram-positive host cell which can readily be engineered to express pyocins by introduction of nucleic acid encoding the desired pyocin, e.g. as described in the Examples below.

Pyocins are typically encoded on plasmids. Thus, host cells may be engineered for pyocin production by introducing a plasmid encoding a pyocin, although other expression vectors or constructs may be employed, including chromosomally-integrated expression constructs.

In some cases, the host cell may be sensitive to the pyocin. In such cases it is desirable that the host cell also comprises nucleic acid encoding a complementary immunity protein (i.e. one capable of antagonising the activity of the pyocin) and is capable of expressing that immunity protein. For example, when pyocins S2, SD2 and AP41 are expressed in *E. coli*, co-expression of an immunity protein is desirable. Pyocins L1 and S5 can typically be expressed in *E. coli* in the absence of an immunity protein. The pyocin and the immunity protein may be encoded on the same expression construct (e.g. plasmid) or on different expression constructs.

Examples of immunity protein sequences include the following:

Pyocin S2 Immunity Protein:

[SEQ ID NO: 25]
MKSKISEYTEKEFLEFVKDIYTNNKKKEPTEESHIQAVLEFKKLTEHPSG

SDLLYYPNENREDSPAGVVKEVKEWRASKGLPGFKAG

Pyocin SD2 Immunity Protein:

[SEQ ID NO: 26]
MSMEMIDIAKRLLASSIDGKIFSEEFFKTWRSERDSGVLAQDDASLGRCL

SLMEGLADSFTEGKKERPGELTEGELKIALSDLLKEYKYI

Pyocin S5 Immunity Protein:

[SEQ ID NO: 27]
MSFKYYWAKFFWGAFFFVLVAWKGSVFPSLASVNPLVVAGLSTILFPFSV

KLVEDFALKYTEREFWVTGFFSETPAKTGLYAVFYLSCYLFSIPLGMVFL

FYKYGKAS

Pyocin AP41 Immunity Protein:

[SEQ ID NO: 28]
MDIKNNLSDYTESEFLEIIEEFFKNKSGLKGSELEKRMDKLVKHFEEVT

SHPRKSGVIFHPKPGFETPEGIVKEVKEWRAANGLPGFKAG

The mechanism by which pyocins are released from the host cell is not well characterised. When expressed in non-*Pseudomonas* host cells, certain pyocins may be naturally secreted and thus may be recovered from the culture medium. For other pyocins, it may be convenient to recover the pyocin from the cell itself, e.g. by an appropriate lysis and purification procedure. The skilled person is well able to design suitable protocols according to their particular needs and the specific cells and proteins involved.

Subjects and Conditions for Treatment

The materials and methods of the present invention are suitable for prophylaxis and/or treatment of infection by *Pseudomonas*, especially *Pseudomonas aeruginosa*, and the bacterial pneumonia associated with such infection.

The infection may be acute or chronic.

*P. aeruginosa* infection of the lower respiratory tract is particularly common in patients with cystic fibrosis (where it represents the leading cause of mortality) and chronic obstructive pulmonary disease (COPD). Other patients with compromised respiratory tract function and/or compromised immune function may also be susceptible to infection, including patients with congestive heart failure, AIDS patients, and patients taking immunosuppressive medications or undergoing other immunosuppressive therapy, e.g. for cancer (especially chemotherapy) rheumatoid arthritis, multiple sclerosis, myasthenia gravis, systemic lupus erythematosus, sarcoidosis, focal segmental glomerulosclerosis, Crohn's disease, Behcet's Disease, pemphigus, ulcerative colitis, etc.

Acute conditions associated with or caused by *Pseudomonas* infection include community-acquired pneumonia and nosocomial infections such as ventilator-associated pneumonia and hospital-acquired pneumonia.

It will be appreciated that, due to variability between clinical strains of *P. aeruginosa*, not all pyocins may be effective against all strains. Factors affecting pyocin effectiveness or toxicity include differential distribution of immunity proteins amongst different strains and genetic variability in the surface receptor bound by the pyocin's targeting portion.

The pyocin to be administered should be effective against one or more of the infecting strains of *P. aeruginosa*. Thus it may be desirable to provide a sample of the infecting strain or strains from a subject, determine the identity of said strain or strains, and select the pyocin(s) to be administered accordingly.

For example, if the infection comprises strain P5, it may be desirable to administer a pyocin other than S2. Similarly, if the infection comprises strain E2, it may be desirable to administer a pyocin other than S2 and AP41. If the infection comprises strain P17, it may be desirable to administer a pyocin other than L1. Of course, as any infection may involve more than one strain of bacterium, it may still be desirable to include these pyocins as part of a cocktail comprising a plurality of pyocins. However, it will usually be advisable also to administer one or more pyocins having activity against the predominant species or strain(s).

Additionally or alternatively, it may be desirable to provide a sample of the infecting strain or strains from a subject, test a pyocin or a plurality of pyocins for toxicity in vitro against one or more of the infecting strains, and select one or more pyocins having appropriate toxicity for use in treating the subject.

The methods described above may comprise the step of obtaining the sample from the subject, or may utilise a sample already obtained.

Typically the subject to be treated is a mammal. The subject is typically human, but may be any other primate (great ape, old world monkey or new world monkey), or a domestic, laboratory or livestock animal, such as a mouse, rat, guinea pig, lagomorph (e.g. rabbit), cat, dog, pig, cow, horse, sheep or goat.

Pharmaceutical Compositions

Delivery of pyocins for the purposes of the invention is by pulmonary administration. The term "pulmonary administration" is intended to encompass any suitable delivery method by which the active agent is delivered to the lungs via the respiratory tract.

The most common methods of pulmonary administration are oral and/or nasal inhalation. As an alternative, intratracheal instillation may be employed, although this is typically not considered a suitable route for clinical administration to human subjects.

The active agents, i.e. S-type pyocins, are typically provided in therapeutic compositions or pharmaceutically acceptable compositions. They may be formulated for pulmonary administration in any suitable manner, e.g. in a liquid or solid (typically powder) form. Formulations may be delivered by any suitable mechanism or delivery device including an inhaler (e.g. metered-dose inhaler, dry powder inhaler) nebuliser (e.g. ultrasonic nebuliser, jet nebuliser, vibrating mesh nebuliser), etc.

Thus the invention further provides a device for pulmonary administration of a therapeutic composition to a subject, the composition comprising an S-type pyocin as described elsewhere in this specification. The device may be an inhaler (e.g. metered-dose inhaler, dry powder inhaler) or nebuliser (e.g. ultrasonic nebuliser, jet nebuliser, vibrating mesh nebuliser).

The compositions for delivery may comprise, in addition to one or more of the active agents, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the precise nature of the formulation and delivery device to be employed.

Liquid compositions generally include an aqueous carrier such as water or physiological saline solution. Dextrose or other saccharide solutions or glycols such as ethylene glycol, propylene glycol or polyethylene glycol may be included.

Emulsions and nano-particle encapsulations, both employing lipids, may also be employed.

Solid (e.g. powder) preparations may utilise carriers such as sugars, cyclodextrins, etc. They may be prepared by any suitable method including spray drying, spray freeze drying, solvent precipitation, jet milling, etc.

In all cases, preservatives, stabilisers, buffers, antioxidants and/or other additives may be included, as required.

Administration is preferably in a "prophylactically effective amount" or a "therapeutically effective amount" (as the case may be, although prophylaxis may be considered therapy), this being sufficient to show benefit to the individual. The actual amount administered, and rate and timecourse of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The inventors have shown that repeated exposure to pyocins does not significantly compromise efficacy of treatment. Thus, a course of treatment may comprise or consist of a single administration or of multiple administrations. A multiple dose regime may comprise or consist of two, three, four, five, or even more individual administrations, e.g. up to ten administrations. Consecutive doses may independently be spaced by any appropriate time interval, e.g. up to 12 hours, up to one day, up to one week, up to 2 weeks, or up to one month.

A composition may be administered alone or in combination with other treatments, either simultaneously or sequentially dependent upon the condition to be treated.

Examples

Methods

Study design. The objectives of this study were to show the efficacy of pyocins in a mouse model of acute *P. aeruginosa lung infection and to show that pyocin treatment in the absence of infection was not harmful. For all experiments 6 week-old, female, murine pathogen free C57/BL6 mice weighing 15-21 g were used (Charles Rivers Laboratories, UK). All mice received food and water ad libitum and were housed in groups during the experiments. Power calculations were used to predetermine sample size (n=6, for all treatment experiments). Mice were culled when required as determined by a scoring system or culled at the pre-determined 24 h time point. All mice, including outliers were included in the statistical analysis. Experiments were either carried out once only or repeated once (defined for each experiment).

Ethics Statement. All animal experiments were performed in accordance with the UK Animals (Scientific procedures) Act, authorized under a UK Home Office License, and approved by the animal project review committee of the University of Glasgow. Animal studies were not randomized and blinding was not possible in this study. The project license number assigned by the animal project review committee of the University of Glasgow was 60/4361.

Cloning and purification of pyocins. The genes encoding pyocin AP41 and its immunity protein (ImAP41) were amplified from the genomic DNA of *P. aeruginosa* C763 by PCR using primers designed to introduce an NdeI site at the start of the pyocin encoding gene (ACA GAT CAT ATG AGC GAC GTT TTT GAC CTT GG) and an XhoI in place of the stop codon of the ImAP41 encoding gene (ACA GAT CTC GAG GCC AGC TTG AA GCC AGG G). The PCR product was digested with NdeI and XhoI and ligated into the corresponding sites of the *E. coli* expression vector pET21a to give pETPyoAP41, which was used for the production of the pyocin AP41-ImAP41 complex in which ImAP41 carries a C-terminal His6-tag. The gene encoding pyocin S5 was similarly amplified from the genomic DNA of strain PA01 using primers designed to introduce and NdeI site at the start of the gene (GAG ACA TAT GTC CAA TGA CAA CGA AGT AC) and an XhoI site after the stop codon (TTT GAC GTC TCG AGT TAA ATG GAT ATT ACA AGA TTG TTT GC) and the digested PCR product ligated into pET15b to give pETPyoS5, which encodes pyocin S5 with an N-terminal His6-tag. Pyocins AP41 and S5 were overexpressed from *E. coli* BL21 (DE3) pLysS carrying the relevant plasmid. Protein production was induced by the addition of 1 mM isopropyl β-D-1-thiogalactopyranoside (IPTG) and the cells were grown at 37° C. for a further 4 h and harvested by centrifugation. Cells were resuspended in 20 mM Tris-HCl, 500 mM NaCl, 5 mM imidazole (pH 7.5) and lysed using an MSE Soniprep 150 (Wolf Laboratories) and the cell debris was separated by centrifugation. The cell-free lysate was applied to a 5-ml His Trap HP column (GE Healthcare) equilibrated in 20 mM Tris-HCl, 500 mM NaCl, 5 mM imidazole (pH 7.5) and eluted over a 5-500 mM imidazole gradient. Remaining contaminants were removed by gel filtration chromatography on a Superdex S200 26/600 column (GE Healthcare). Pyocin L1 and the pyocin S2-ImS2 complex were purified as described previously ([25,32]). Pyocins were concentrated using a centrifugal concentrator (Vivaspin 20) with a molecular weight cut off of 5 kDa and dialysed overnight into phosphate buffered saline, pH 7.3. Contaminating lippopolysaccharide (LPS) was removed using 1 ml gravity flow endotoxin removal columns (Thermo Scientific) and proteins were filter sterilised using a 0.2 μm syringe filter. Pyocins were aliquoted and stored at −80° C. until required.

Pyocin sensitivity assays: overlay spot plate method. Soft agar overlay spot plates were performed using the method of [35]. 150 μl of test strain culture at $OD_{600\,nm}$=0.6 was added to 6 ml of 0.8% soft agar and poured over an LB agar plate. 5 μl of bacteriocin, lung homogenate or blood at varying concentrations was spotted onto the plates and incubated for 24 h at 37° C.

Pyocin delivery. For pyocin delivery to the uninfected lung, 25 μl of pyocin at 3 mg ml$^{-1}$ (n=4) was delivered via the intranasal route after induction of anaesthesia with isofluorane. Mice were culled at 24 h by carbon dioxide asphyxiation. A cannula was inserted into the trachea and lungs were fixed in situ by gentle infusion of 10% formalin solution at a constant pressure for 2 min. The lungs were then removed and placed in a container with more fixative. Histology processing and hematoxylin and eosin (H&E) staining was carried out by the Veterinary Diagnostic Services Laboratory within the School of Veterinary Medicine at the University of Glasgow. High-resolution whole slide images were captured on the Leica SCN400 slide scanner and slides were scored blind by two independent assessors for peribronchial infiltrate and alveolar involvement.

Model of acute lung infection. Female C57/BL6 mice were inoculated intranasally with 25 μl of bacterial culture containing approximately $10^7$ CFU of the selected *P. aeruginosa* strain[36]. Antibiotic treatments were administered at either 6 h pre-infection or 1 h post-infection and were administered only once. Pyocins or tobramycin dissolved in PBS were administered via intranasal administration as described above. Two different end-points were used in these experiments. In order to determine a reduction in the bacterial load of the lungs compared to the untreated controls, all mice in the experiment were culled by carbon dioxide asphyxiation at the same time; 4-6 h post infection. To determine if mice could survive infection after pyocin or tobramycin treatment, mice were monitored closely, culled by carbon dioxide asphyxiation when required as determined by a scoring system or culled at the pre-determined 24 h time point. Uninfected mice, treated with pyocins, were used as controls in the first series of experiments in order to ensure no adverse effects from pyocin treatment. These controls were stopped in later experiments in order to reduce the number of animals used, once it was clear that the pyocins were not harmful. For CFU determination, lungs were removed aseptically and kept on ice in 750 μl of PBS until homogenised. Serial 10-fold dilutions of the homogenised lung were plated on *Pseudomonas* selective agar (20 g peptone, 1.5 g $K_2HPO_4$, 1.5 g $MgSO_4 \cdot 7H_2O$, 10 ml glycerol, 15 g agar, 0.025 g Irgasan per litre) and incubated at 37° C. for 24 h and then room temperature for 24 h before the colonies were counted.

Repeated pyocin exposure. Pyocin S5 or PBS was given three times, two weeks apart with administration either via intranasal route (referred to as I.N. groups) or intraperitoneal route (referred to as I.P. groups). For I.N. administration the groups were: PBS and pyocin S5 (75 μg; 25 μl at 3 mg ml$^{-1}$). For I.P. administration the group was pyocin S5 (75 μg; 100 μl at 750 μg ml$^{-1}$). The PBS I.N. group served as the control group for the I.P. group. Thirteen weeks after the first exposure mice (n=5) were infected intranasally with *P. aeruginosa* P8 (I.N group infected with 1.4×10$^7$ CFU, I.P group infected with 5.0×10$^6$ CFU) and treated intranasally one hour post-infection with 75 μg of pyocin S5 or PBS, as described previously.

Determination of pyocin S5-specific antibody titers by indirect ELISA. For analysis of IgG and IgA responses, blood was obtained by cardiac puncture immediately after carbon dioxide asphyxiation. Serum was obtained by centrifugation of samples at 13,500 g for 10 min followed by collection of the supernatant. Serum was stored at −80° C. Greiner 96-well plates (MaxiSorp) were coated with purified recombinant pyocin S5 (7.5 μg ml$^{-1}$, 50 μl/well) protein in PBS overnight at 4° C. The plates were washed three times with phosphate buffered saline+0.05% TWEEN20 (PBST) and then blocked for 1 h at 37° C. with 150 μl of blocking buffer (1% bovine serum albumin (BSA) in PBS). After washing, five-fold serially diluted samples were added, starting at a dilution of 1/50 in blocking buffer, and incubated for 2 h at 37° C. Serum from mice given pyocin S5+Freunds complete/incomplete subcutaneously three times over four weeks was used as a positive control and uncoated wells were used as negative controls. Serum from individual mice were analysed and replicate samples were carried out on separate days. After washing with PBST, 50 μl of anti-mouse IgG (Fc specific)-peroxidase antibody ((1/1000 dilution) Sigma, UK) or anti-mouse IgA (α-chain specific)-peroxidase antibody ((1/250 dilution) Sigma, UK) in PBST/0.1% BSA was added and plates were incubated for 1 h at 37° C. Plates were developed using SIGMAFAST OPD (o-Phenylenediamine dihydrochloride) tablets (Sigma, UK) and reactions were stopped using 3 M HCl. Optical densities (ODs) were read at 450 nm using a FLUOstar OPTIMA plate reader (BMG labtech, Germany).

Statistics. Due to small sample sizes non-parametric tests were used for analysis. The Kruskal-Wallis one-way analysis of variance method was used to test if samples originated from the same distribution. One-sided Mann-Whitney U tests with a significance threshold of $P \leq 0.05$, adjusted for multiple comparisons using the Bonferroni correction, was then used to analyse the specific sample pairs for significant differences. All mice, including outliers were included in the statistical analysis.

Results

Pyocins are Stable in the Murine Lung and do not Cause Inflammation or Tissue Damage To determine if pyocins can be effectively delivered to the lungs and if they are stable in this environment, recombinant pyocins S2, S5, AP41 and L1 were administered intranasally to healthy C57/BL6 mice. After a 24 h incubation period, the postcaval lobe was removed from treated mice, homogenized and tested for the presence of active pyocin by spotting onto a growing lawn of P. aeruginosa (strain P8 for most pyocins and P17 for pyocin S2). Killing of P. aeruginosa was detected with lung homogenates from pyocin L1, S2 and S5 treated mice, but was not observed in homogenates from pyocin AP41 or PBS treated mice (data not shown). These data indicate that pyocins are well distributed through the lung after intranasal administration and in the case of pyocins L1, S2 and S5 are stable in this environment. For pyocin AP41, activity was not detected. This could be due to the sensitivity of the P. aeruginosa indicator strain or could indicate that this pyocin may be more rapidly degraded than the other tested pyocins in vivo. To ascertain if pyocins could be harmful to the host, pyocins were again administered intranasally and after 24 h pyocin treated lungs were fixed. Lung tissues visualised using hematoxylin and eosin staining were then scored for peribronchial infiltrate and alveolar macrophage involvement. The pyocin treated lungs showed no signs of such features, and were indistinguishable from the PBS treated tissue, indicating that the administration of a single high-concentration dose of any of this diverse group of protein antibiotics does not lead to overt inflammation or tissue damage (data not shown).

Pyocins can Afford Protection Against Lethal P. aeruginosa Infections

To determine if pyocins are sufficiently active to reduce bacterial load in the lung, pyocins S2, S5, AP41 and L1 (3 mg ml$^{-1}$), or PBS for control mice, were administered intranasally 6 h pre-infection with a normally lethal dose of P. aeruginosa P8 (approx $10^7$ CFU). All mice were culled 4 h post-infection and viable bacterial counts from lung homogenates determined (FIG. 1a). All pyocins reduced bacterial load, although at this time point differences in efficacy were noted, with pyocins S2, AP41 and L1 reducing bacterial numbers by approximately 25-fold, 650-fold and 1500-fold, respectively. In the case of pyocin S5, no viable bacteria were recovered.

In order to determine if pyocin activity is sufficient to afford protection against a normally lethal dose of P. aeruginosa, mice were similarly pre-treated with pyocins 6 h pre-infection with P. aeruginosa P8, monitored for sickness and culled on reaching a pre-determined severity of illness clinical score. Five out of six of the PBS control mice were culled at 5 h post-infection whereas all pyocin treated mice survived to the endpoint of the experiment at 24 h. Viable bacterial counts at this time point indicated a similar killing activity for pyocins S2, AP41 and L1, which all significantly reduced bacterial counts more than 10,000-fold. Again, at this time point no viable bacteria were recovered from pyocin S5 treated mice (FIG. 1b).

Figure 7:
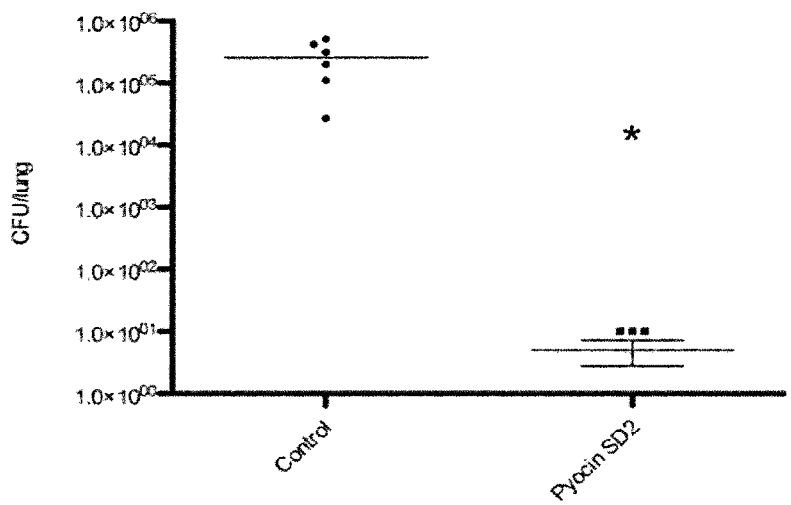
FIG. 7. Pyocin SD2 for the treatment of *P. aeruginosa* PA01 infected mice. Mice treated 1 h post-infection with pyocin SD2 at a stock concentration of 3 mg ml$^{-1}$. Control mice were culled at 6 h post-infection and pyocin SD2 treated mice survived to 24 h. Bars represent Mean±SEM, * denotes statistical significance for comparison of treatment versus control by a one-sided Mann-Whitney U test with Bonferroni correction applied.

A similar experiment was performed using pyocin SD2. C57/BL6 mice (n=6) were infected with approx $1.5 \times 10^7$ CFU of P. aeruginosa PA01 and treated 1 h post-infection with pyocin SD2 at 3 mg ml$^{-1}$. Infected mice were monitored for sickness and culled if a sufficient clinical score was reached, or alternatively at the endpoint of the experiment, 24 h post-infection. Pyocin SD2 treated mice survived to the endpoint of the experiment at 24 h, control mice were culled 6 h post infection. The bacterial load of the lungs was determined and control mice had approx $2 \times 10^5$ CFU/lung, 6 h after infection. For pyocin SD2 mice, either no colonies or 10 CFU/lung were recovered 24 h post-infection (FIG. 7).

Figure 5:
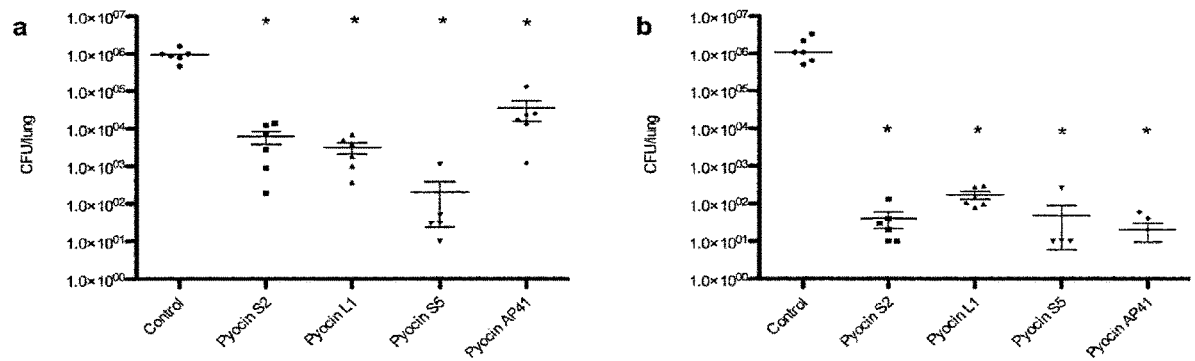
FIG. 5. Biological repeats of experiments in FIGS. 1 (c) and (d). *P. aeruginosa* P8 bacterial recovery from pyocin treated mice. All pyocins were given at 3 mg ml$^{-1}$. Bacterial counts determined by CFU counts of homogenized lungs. Counts from pyocin treated mice were compared to those from PBS treated mice (a) Mice treated with pyocin 1 h post-infection, all mice culled 4.5 h post-infection (b) Mice treated with pyocin 1 h post-infection, pyocin treated mice survived to 24 h. Bars represent Mean±SEM, * denotes statistical significance for comparison of treatment versus control by a one-sided Mann-Whitney U test with Bonferroni correction applied.

The ability of pyocins to reduce bacterial numbers on administration post-infection was then determined. P. aeruginosa P8 infected mice were treated 1 h post-infection with pyocins S2, S5, AP41 and L1 at 3 mg ml$^{-1}$. In these experiments mice were culled at 4.5 h post-infection and bacterial counts from lung homogenates were compared to PBS treated controls. Similar to the pre-treatment experiments, pyocin S5 showed greatest efficacy in reducing bacterial numbers, although in this experiment viable bacteria were recovered from three out of six S5 treated mice. Pyocins L1, S2, and AP41 significantly reduced the bacterial load by approximately 20-, 80- and 130-fold, respectively (FIG. 1c). This experiment was repeated and again all pyocin treated groups showed significantly reduced bacterial counts (FIG. 5a).

To determine if pyocin treatment post-infection affords protection against lethal P. aeruginosa infection, mice were similarly infected with P. aeruginosa P8 and treated 1 h post-infection with pyocins S2, S5, AP41 and pyocin L1 at 3 mg ml$^{-1}$. Infected mice were monitored for sickness and culled if sufficient clinical score were reached, or alternatively at the endpoint of the experiment, 24 h post-infection. All PBS treated mice were culled at 4.5 h post-infection and all pyocin treated mice survived to the endpoint of the experiment at 24 h. The bacterial load of the lungs was determined and again pyocin S5 showed the greatest efficacy with no bacteria recovered from any of the six pyocin S5 treated mice. In addition, pyocins S2, L1 and AP41 were also highly effective in this model significantly reducing bacterial counts in excess of 4-log units (FIG. 1d). This experiment was repeated and again all pyocin treated mice survived to 24 h and bacterial counts were similarly significantly reduced (FIG. 5b). Thus, pyocins are highly effective in reducing bacterial load in the lung and are able to afford protection against a lethal P. aeruginosa infection when administered pre- and post-infection.

Since strains of P. aeruginosa are phenotypically diverse, we tested the efficacy of the pyocins against three additional isolates: P. aeruginosa P17 and P. aeruginosa P5 (mucoid), both from cystic fibrosis patients and P. aeruginosa E2, an environmental isolate. Pyocin S2 was not active against P. aeruginosa P5 or P. aeruginosa E2 in vitro therefore was not used to treat these strains in vivo and similarly pyocin L1 was not used against P. aeruginosa P17. All three P. aeruginosa strains showed levels of virulence similar to that of P. aeruginosa P8 in the model of acute lung infection and P. aeruginosa P5, P17 and E2 infected controls all required culling at 4.5 h, 4 h and 5.5 h post-infection, respectively.

Pyocin S5, L1 and S2 treated mice infected with *P. aeruginosa* P17, P5 or E2 all survived until the 24 h endpoint of the experiment and viable bacterial counts were either reduced to significantly low levels or absent (Table 1). In contrast, treatment of *P. aeruginosa* E2 with pyocin AP41 failed to afford protection and these mice were culled at 5.5 h post-infection. Lung homogenates from *P. aeruginosa* E2-infected AP41-treated mice contained high levels of viable bacteria, reduced only 10-fold relative to control mice (Table 1). Pyocin AP41 treatment, however, was successful for *P. aeruginosa* P5 infected mice and for five out of six of the *P. aeruginosa* P17 infected mice. Thus, pyocins show strong efficacy against diverse strains of *P. aeruginosa* with pyocin S5 treatment displaying the largest effect on reducing bacterial load.

TABLE 1

Pyocin treatment for a range of *P. aeruginosa* isolates. Mice were infected with a lethal dose of *P. aeruginosa*. Untreated mice were culled 4 h-5.5 h post infection. Pyocin treated mice (3 mg ml$^{-1}$) survived to 24 h.

| Treatment | P5 | P17 | E2 |
|---|---|---|---|
| No treatment | $1.7 \times 10^5$ CFU/lung | $4.4 \times 10^5$ CFU/lung | $1.5 \times 10^5$ CFU/lung |
| Pyocin L1 | 40 | X | No colonies detected |
| Pyocin S2 | X | No colonies detected | X |
| Pyocin AP41 | No colonies detected | No colonies detected⁺ | $1.3 \times 10^4$ CFU/lung* |
| Pyocin S5 | No colonies detected | No colonies detected | No colonies detected |

*Mice culled at same time as control.
⁺1 mouse coughed up AP41 treatment and was culled at 4 h post-infection, bacterial count $1.3 \times 10^5$ CFU/lung.
X—Pyocin was not used against this strain.

Figure 2:
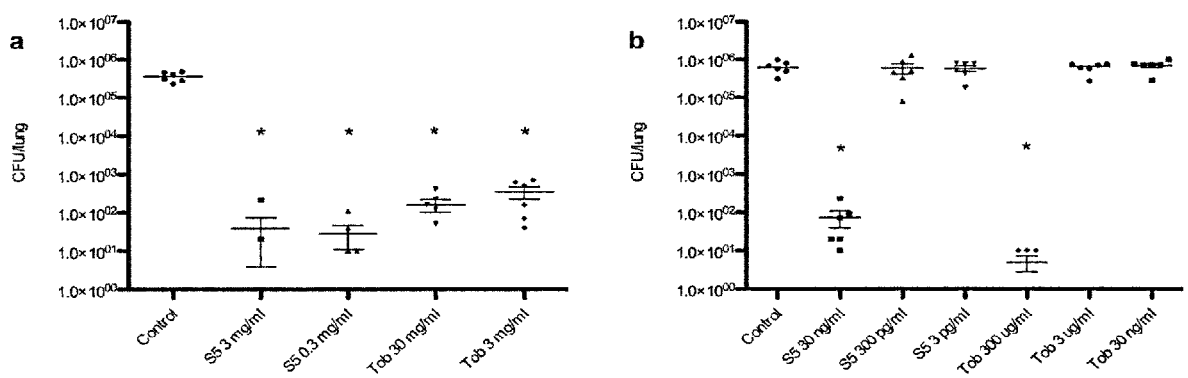
FIG. 2. Pyocin S5 and tobramycin treatment of *P. aeruginosa* P8 infected mice. (A) Mice treated 1 h post-infection, all mice culled 4.5 h post-infection (B) Mice treated 1 h post-infection, S5 30 ng ml$^{-1}$ and tobramycin 300 µg ml$^{-1}$ mice survived to 24 h. All other mice culled 5.5 h post-infection. Bars represent Mean±SEM, * denotes statistical significance for comparison of treatment versus control by a one-sided Mann-Whitney U test with Bonferroni correction applied.
Figure 6:
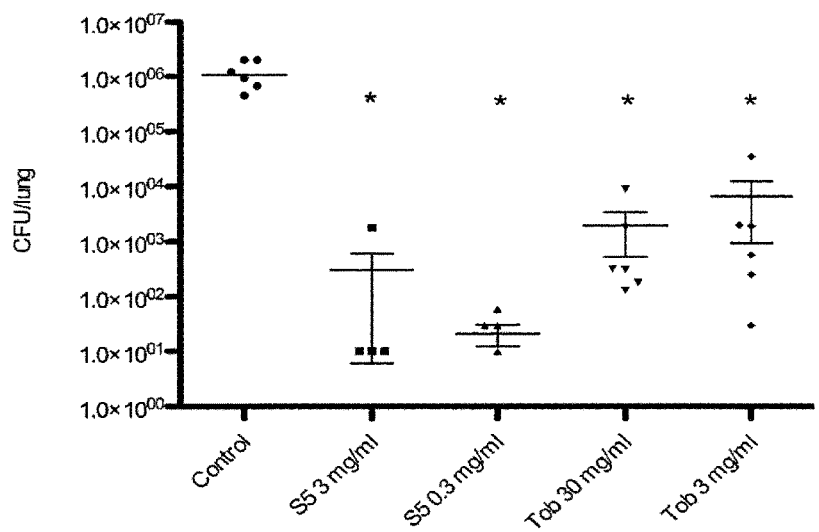
FIG. 6. Repeat of experiment in FIG. 2 (*a*). Pyocin S5 and tobramycin treatment of *P. aeruginosa* P8 infected mice. Mice treated 1 h post-infection, all mice culled 4.5 h post-infection. Bars represent Mean±SEM, * denotes statistical significance for comparison of treatment versus control by a one-sided Mann-Whitney U test with Bonferroni correction applied.

Pyocin S5 Shows Improved Killing of *P. aeruginosa* in the Murine Lung Compared to Tobramycin To compare pyocin efficacy directly with a current front-line treatment, we compared pyocin S5 with tobramycin, which is widely used as an inhaled treatment for *P. aeruginosa* lung infection in patients with cystic fibrosis. Mice were infected as before with *P. aeruginosa* P8 and treated 1 h post-infection with either tobramycin at 30 or 3 mg ml$^{-1}$ or pyocin S5 at 0.3 or 3 mg ml$^{-1}$, culled 4.5 h post-infection and viable bacterial counts determined from lung homogenates. All four treatments significantly reduced the bacterial load compared to the PBS controls. Pyocin S5 at both concentrations reduced the bacterial load to a greater extent than tobramycin (FIG. 2a). This experiment was repeated and again pyocin S5 reduced bacterial counts to a greater extent than tobramycin (FIG. 6). To determine the relative potency of pyocin S5 compared to tobramycin, *P. aeruginosa* P8 infected mice were treated with pyocin S5 at 30 ng ml$^{-1}$, 300 µg ml$^{-1}$ or 3 µg ml$^{-1}$ and tobramycin at 300 µg ml$^{-1}$, 3 µg ml$^{-1}$ or 30 ng ml$^{-1}$. Groups treated with pyocin S5 at 30 ng ml$^{-1}$ and tobramycin at 300 µg ml$^{-1}$ survived to 24 h, all other groups were culled 5.5 h post-infection due to the severity of the infection. 24 h post-infection both pyocin S5 at 30 ng ml$^{-1}$ and tobramycin at 300 µg ml$^{-1}$ had significantly reduced the bacterial counts compared to the PBS controls (FIG. 2b). These results show that the lowest concentration at which pyocin S5 is effective lies between 30 ng ml$^{-1}$ and 300 pg ml$^{-1}$ and the lowest concentration at which tobramycin is effective lies between 300 µg ml$^{-1}$ and 3 µg ml$^{-1}$. Pyocin S5 is therefore at least 100-fold more potent than tobramycin in this model of infection (Table 2).

TABLE 2

Minimum concentration of pyocin tested that affords protection against *P. aeruginosa* P8 infection. The lowest active concentration tested represents the lowest concentration tested with which the treated mice survived to 24 h.

| Pyocin | Lowest active concentration tested | Corresponding molarity |
|---|---|---|
| Pyocin L1 | 30 µg ml$^{-1}$ | 1.06 µM |
| Pyocin S2 | 30 µg ml$^{-1}$ | 358 nM |
| Pyocin AP41 | 30 µg ml$^{-1}$ | 319 nM |
| Pyocin S5 | 30 ng ml$^{-1}$ | 535 pM |
| Tobramycin | 300 µg ml$^{-1}$ | 641 µM |

After ascertaining that pyocin S5 is effective in this model at a concentration lower than 1 nM, we tested the efficacy of pyocins S2, L1 and AP41 at lower concentrations than previously used. All three pyocins were used at 300 µg ml$^{-1}$ and 30 µg ml$^{-1}$. Due to the severity of symptoms three of the six mice treated with pyocin L1 at 30 µg ml$^{-1}$ and PBS control mice were culled at 6 h post-infection. All mice treated with pyocins S2 and AP41 at both concentrations and mice treated with pyocin L1 at 300 µg ml$^{-1}$ survived until the endpoint of the experiment at 24 h post-infection (Table S1). Thus against *P. aeruginosa* P8, the minimum effective concentration of pyocins S2 and AP41 is ≤30 µg ml$^{-1}$ and the minimum effective concentration of pyocin L1 is between 30 and 300 µg ml$^{-1}$. Table Si shows that all pyocins tested in vivo displayed a potency that was comparable to or greater than tobramycin.

Pyocin Tolerance and Mitigation Strategies

Figure 3:
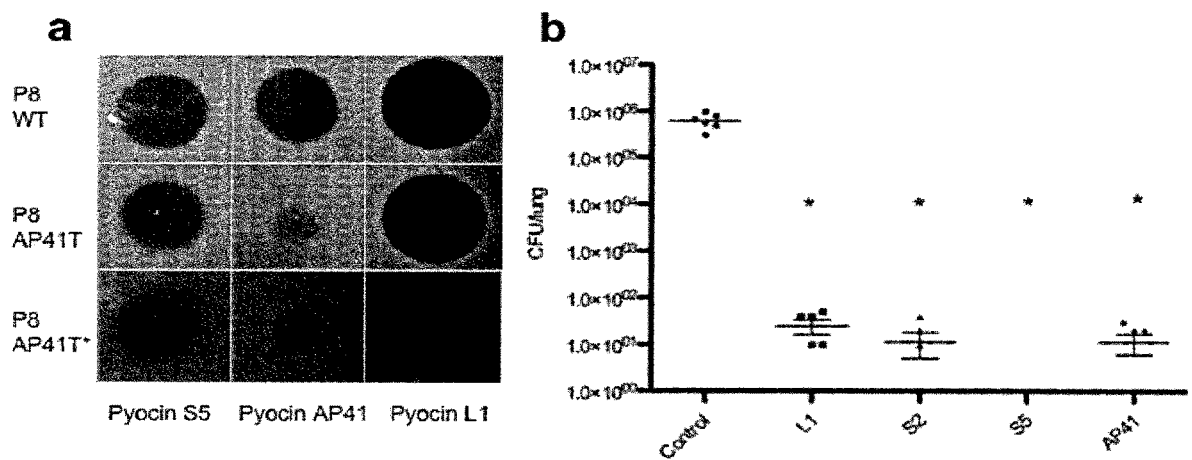
FIG. 3. Acquired tolerance to pyocins can be overcome by treating with a range of pyocins. (a) Spot tests to determine cytotoxic activity of pyocins S5, AP41 and L1. Purified protein at 200 µg ml$^{-1}$ was spotted onto a growing lawn of bacteria. Clear zones indicate pyocin cytotoxicity. P8AP41T is an AP41 tolerant strain of P8 and P8AP41T* is strain P8AP41T recovered from untreated control mice shown in (b). (b) Bacterial counts for mice infected with P8AP41T shown in (a), then treated 1 h post-infection with pyocins at 3 mg ml$^{-1}$. Pyocin treated mice survived to 24 h. No colonies were recovered from pyocin S5 treated mice. Bars represent Mean±SEM, * denotes statistical significance for comparison of treatment versus control by a one-sided Mann-Whitney U test with Bonferroni correction applied.

In order to determine if pyocin tolerance or resistance was acquired upon pyocin treatment in vivo, viable bacteria recovered from mice that survived infection to the 24 h end-point, in all experiments discussed in this work, were tested for pyocin susceptibility. From these experiments no pyocin resistant colonies were isolated. However, we obtained a single isolate (P8AP41T) from pyocin AP41 (3 mg ml$^{-1}$ post-infection) treated bacteria that showed increased tolerance (approximately 1000-fold) to pyocin AP41. Importantly, sensitivity to pyocins S5 and L1 were unaffected in vitro in this pyocin AP41-tolerant strain (FIG. 3a) and this was also shown to be the case in vivo when mice were infected with P8AP41T. In contrast to PBS controls, which were culled 6 h post-infection, pyocin treated (3 mg ml$^{-1}$) P8AP41T infected mice survived until the endpoint of the experiment at 24 h and had significantly reduced bacterial numbers in lung homogenates (FIG. 3b). Interestingly, this applied not only to treatment with pyocins L1, S2, S5, but also to treatment with pyocin AP41, indicating that this pyocin AP41-tolerant mutant can still be successfully treated with pyocin AP41 at high concentrations. Pyocin susceptibility testing showed that this strain remained tolerant to pyocin AP41 during infection (FIG. 3a).

Figure 4:
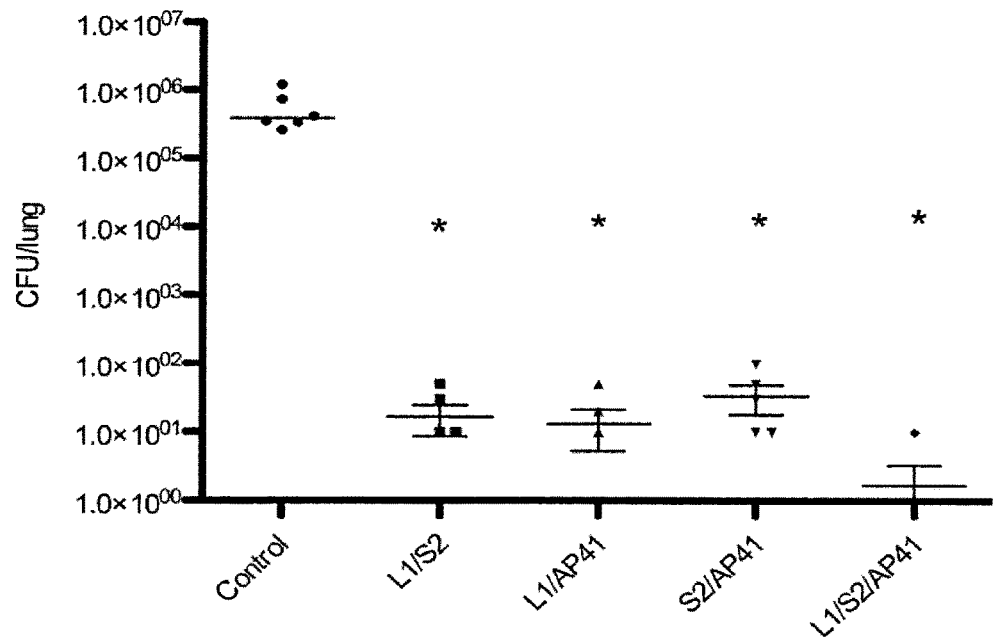
FIG. 4. Pyocin combinations for the treatment of *P. aeruginosa* P8 infected mice. Mice treated 1 h post-infection with pyocins at stock concentrations of 300 µg ml$^{-1}$; pyocin treated mice survived to 24 h. Bars represent Mean±SEM, * denotes statistical significance for comparison of treatment versus control by a one-sided Mann-Whitney U test with Bonferroni correction applied.

As all four pyocins used in this study parasitise different nutrient uptake receptors in *P. aeruginosa* an obvious strategy to prevent the occurrence of pyocin resistance is to use 'pyocin cocktails' consisting of two or more pyocins in combination. We therefore tested the efficacy of combinations of two or more pyocins in the acute lung infection model with *P. aeruginosa* P8. The following pyocin combinations were tested: L1/S2, L1/AP41, S2/AP41 and L1/S2/AP41 with all pyocins at 300 µg ml$^{-1}$. PBS control mice were culled 4.5 h post-infection and all pyocin treated mice survived until 24 h. Viable bacteria were recovered at a low level from pyocin treated mice and for the combination of L1/S2/AP41, bacteria were recovered from only one of six treated mice, indicating that pyocin combinations show enhanced efficacy over the use of individual pyocins (FIG. 4). No pyocin resistance or tolerance was observed for bacteria recovered after treatment with multiple pyocins.

Figure 8:
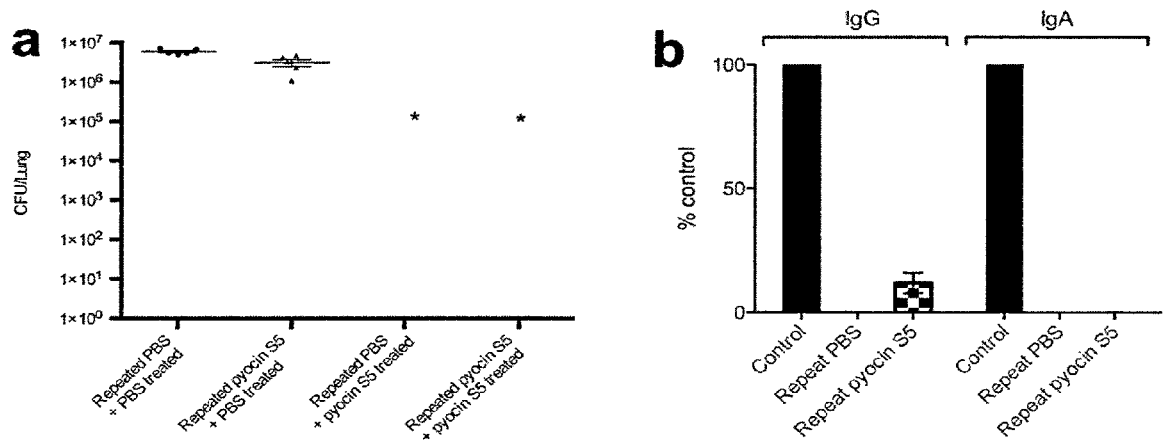
FIG. 8. Pyocin S5 can afford protection against lethal *P. aeruginosa* infections in the presence of pyocin S5 antibodies. (a) Bacterial counts for mice repeatedly exposed to pyocin S5 or PBS intranasally and subsequently infected with *P. aeruginosa* P8 and treated with pyocin S5 or PBS post infection. Bacterial counts determined by CFU counts from homogenised lungs. Multiple doses of pyocin S5 (75 µg/dose) were administered three times, two weeks apart over four weeks. At thirteen weeks, mice were infected with *P. aeruginosa* P8 and treated with pyocin S5 (75 µg) or PBS 1 h post-infection. * Denotes statistical significance for comparison of treatment versus control by a one-sided Mann-Whitney U test with Bonferroni correction applied. (b) IgG and IgA serum levels for mice repeatedly exposed to pyocin S5 or PBS (as described in a). The control group were administered pyocin S5 (75 µg/dose) with Freunds complete/incomplete subcutaneously three times, two weeks apart. Bars represent Mean±SEM. (c) and (d) as for (a) and (b) except mice were repeatedly exposed to pyocin S5 via the intraperitoneal (I.P.) route.
Figure 8:
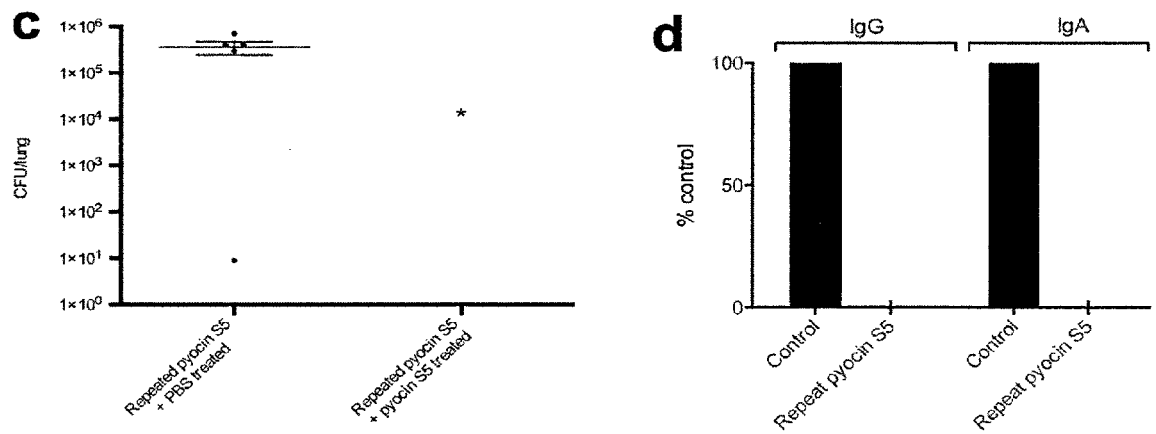

Pyocin S5 can Afford Protection Against Lethal *P. aeruginosa* Infections in the Presence of Pyocin S5 Antibodies To ascertain if repeated exposure to pyocins gives rise to an antibody response that is detrimental to treatment, mice were repeatedly exposed to pyocin S5 to induce an antibody response and the efficacy of pyocin treatment was determined as before after infection with *P. aeruginosa* P8. Pyocin S5 was administered three times, with two weeks between each administration, either via the intranasal route (I.N.) or the intraperitoneal (I.P.) route. Thirteen weeks after the first treatment, mice (n=5) were infected intranasally with *P. aeruginosa* P8 (I.N. group infected with $1.4 \times 10^7$ CFU, I.P. group infected with $5.0 \times 10^6$ CFU) and treated intranasally 1 h post-infection with 75 µg of pyocin S5 or PBS. A control group administered only PBS intranasally prior to infection was also included. For the I.N. groups, all pyocin S5 treated mice survived to the 24 h time-point, while all PBS-treated mice were culled 5 h post-infection due to severity of symptoms. The bacterial load of the lungs was determined and no viable bacteria were recovered from any of the pyocin S5 treated mice (FIG. 8a). The levels of pyocin-S5 specific IgG and IgA were analysed for each mouse. There were no IgA antibodies detected in these mice; however there were low levels of IgG present in the mice previously exposed to pyocin S5 (10-fold less than the Freunds complete/incomplete control group) (FIG. 8b). For the mice repeatedly exposed to pyocin S5 via the I.P. route, mice treated with pyocin S5 intranasally post-infection all survived to the 24 h time-point and PBS-treated mice were culled 5 h post-infection due to the severity of symptoms. The bacterial load of the lungs was determined and no viable bacteria were recovered from any of the pyocin S5 treated mice (FIG. 8c). The pyocin S5-specific IgG levels were very low in the pyocin S5 only group (1000-fold less than the Freunds complete/incomplete control group) and no pyocin S5-specific IgA was detected (FIG. 8d). Thus, pyocin S5 shows strong efficacy after repeated administration and in the presence of pyocin-S5 specific antibodies.

Discussion

In this work we have shown that pyocins are highly effective in reducing bacterial load and affording protection in a lethal model of acute *P. aeruginosa* lung infection when delivered directly to the lung. Notably, pyocin S5 was shown to afford protection at a concentration that is at least 100-fold lower than the minimum effective concentration of tobramycin, an antibiotic that is widely used to treat *P. aeruginosa* lung infections. All pyocins tested in vivo displayed a potency that was comparable to or greater than tobramycin. In addition, the administration of these highly stable, chromosomally encoded pyocins at high concentrations did not lead to overt inflammation or tissue damage in the lung. Taken together, these data suggest that pyocins have the potential to make useful therapeutics for the treatment of *P. aeruginosa* lung infections. These include *P. aeruginosa* infections associated with cystic fibrosis, hospital-acquired and ventilator-associated pneumonia and chronic obstructive pulmonary disease (COPD), all of which are areas of current unmet medical need[10,11]. Indeed, related colicin-like and lectin-like bacteriocins may also make useful therapeutics for the treatment of respiratory infections with frequently antibiotic-resistant pathogens such as *Klebsiella pneumoniae* and *Burkholderia* spp.

In addition to their potency, an additional advantage of the colicin-like bacteriocins is their narrow spectrum of killing. This allows for the possibility of successfully treating bacterial infections while leaving the normal bacterial flora intact. Well-established complications associated with the use of broad-spectrum antibiotics and dysbiosis include antibiotic-associated diarrhea and *Clostridium difficile* infection[26,27]. More recently, microbial imbalances have been suggested to play a role in a range of chronic diseases such as Crohn's disease, diabetes, obesity and rheumatoid arthritis[28-31].

Of the pyocins tested in this study, the receptors for pyocins S2 and S5 are known to be the TonB-dependent iron-siderophore receptors FpvAI and FptA, respectively[21,22] and the receptor for pyocin L1 has recently been shown to be the common polysaccharide antigen (CPA) of lipopolysaccharide[32]. However, the receptor for pyocin AP41 remains to be discovered. FptA and the CPA are known to be widely distributed among strains of *P. aeruginosa*[33] and interestingly CPA production by *P. aeruginosa* has been shown to be up-regulated in the cystic fibrosis lung[34], meaning that pyocin L1 may be active against strains in vivo for which no in vitro activity can be detected. Using a 'cocktail' of pyocins that target different cell surface receptors will reduce the chances of acquired pyocin resistance and also reduce the probability of resistance imparted by the presence of a pyocin-specific immunity protein genes in pyocin-producing strains. However, inherent pyocin-specific immunity is not a great limitation of these antimicrobials as pyocins AP41 and S5 are active against 87% of strains in a collection of diverse environmental and clinical isolates.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

REFERENCES

1 Souli, M., Galani, I., & Giamarellou, H., (2008) Emergence of extensively drug-resistant and pandrug-resistant Gram-negative bacilli in Europe. *Eurosurveillance*. 13, 19045-19045.

2 Vila, J. & Luis Martinez, J., Clinical Impact of the Over-Expression of Efflux Pump in Nonfermentative Gram-Negative Bacilli, Development of Efflux Pump Inhibitors. (2008) *Current Drug Targets.* 9, 797-807.

3 Nikaido, H., Molecular basis of bacterial outer membrane permeability revisited. (2003) *Microbiol Mol Biol Rev.* 67, 593-656.

4 Flamm, R. K. et al., Factors associated with relative rates of antibiotic resistance in *Pseudomonas aeruginosa* isolates tested in clinical laboratories in the United States from 1999 to 2002. (2004) *Antimicrob Agents Chemother.* 48, 2431-2436.

5 Mah, T. F. et al., A genetic basis for *Pseudomonas aeruginosa* biofilm antibiotic resistance. (2003) *Nature.* 426, 306-310.

6 Drenkard, E. & Ausubel, F. M., *Pseudomonas* biofilm formation and antibiotic resistance are linked to phenotypic variation. (2002) *Nature.* 416, 740-743.

7 Livermore, D. M., Multiple mechanisms of antimicrobial resistance in *Pseudomonas aeruginosa*: Our worst nightmare? (2002) *Clinical Infectious Diseases*. 34, 634-640.
8 Cystic Fibrosis Trust Annual data report 2011,UK CF Registry, 2013.
9 Chastre, J. & Fagon, J. Y., Ventilator-associated pneumonia. (2002) *American Journal of Respiratory and Critical Care Medicine*. 165, 867-903.
10 Planquette, B. et al., *Pseudomonas aeruginosa* Ventilator-associated Pneumonia Predictive Factors of Treatment Failure. (2013) *American Journal of Respiratory and Critical Care Medicine*. 188, 69-76.
11 Martinez-Solano, L., Macia, M. D., Fajardo, A., Oliver, A., & Martinez, J. L., Chronic *Pseudomonas aeruginosa* Infection in Chronic Obstructive Pulmonary Disease. (2008) *Clinical Infectious Diseases*. 47, 1526-1533.
12 Murphy, T. F. et al., *Pseudomonas aeruginosa* in chronic obstructive pulmonary disease. (2008) *American Journal of Respiratory and Critical Care Medicine*. 177, 853-860.
13 Payne, D. J., Gwynn, M. N., Holmes, D. J., & Pompliano, D. L., Drugs for bad bugs: confronting the challenges of antibacterial discovery. (2007) *Nat Rev Drug Discov*. 6, 29-40.
14 Bumann, D., Has nature already identified all useful antibacterial targets? (2008) *Current Opinion in Microbiology*. 11, 387-392.
15 Shlaes, D. M., Sahm, D., Opiela, C., & Spellbergc, B., The FDA Reboot of Antibiotic Development. (2013) *Antimicrob Agents Chemother*. 57, 4605-4607.
16 Michel-Briand, Y. & Baysse, C., The pyocins of *Pseudomonas aeruginosa*. (2002) *Biochimie*. 84, 499-510.
17 Cascales, E. et al., Colicin biology. (2007) *Microbiol Mol Biol Rev*. 71, 158-229.
18 Parret, A. H. A. & De Mot, R., Bacteria killing their own kind: novel bacteriocins of *pseudomonas* and other gamma-proteobacteria. (2002) *Trends Microbiol*. 10, 107-112.
19 Ferguson, A. D. & Deisenhofer, J., TonB-dependent receptors—structural perspectives. (2002) *Biochimica Et Biophysica Acta—Biomembranes*. 1565, 318-332.
20 Kleanthous, C., Swimming against the tide: progress and challenges in our understanding of colicin translocation. (2010) *Nat. Rev. Microbiol*. 8, 843-848.
21 Elfarash, A., Wei, Q., & Cornelis, P., The soluble pyocins S2 and S4 from *Pseudomonas aeruginosa* bind to the same FpvAI receptor. (2012) *MicrobiologyOpen*. 1, 268-275.
22 Elfarash, A. et al., Pore-forming pyocin S5 utilizes the FptA ferripyochelin receptor to kill *Pseudomonas aeruginosa*. (2014) *Microbiology*. 160, 261-269.
23 Housden, N. G. et al., Intrinsically Disordered Protein Threads Through the Bacterial Outer-Membrane Porin OmpF. (2013) *Science*. 340, 1570-1574.
24 Baysse, C. et al., Uptake of pyocin S3 occurs through the outer membrane ferripyoverdine type II receptor of *Pseudomonas aeruginosa*. (1999) *J Bacteriol*. 181, 3849-3851.
25 Smith, K. et al., Activity of Pyocin S2 against *Pseudomonas aeruginosa* Biofilms. (2012) *Antimicrob Agents Chemother*. 56, 1599-1601.
26 Gorkiewicz, G., Nosocomial and antibiotic-associated diarrhoea caused by organisms other than *Clostridium difficile*. (2009) *Int J Antimicrob Agents*. 33, S37-S41.
27 Carroll, K. C. & Bartlett, J. G., Biology of *Clostridium difficile*: Implications for Epidemiology and Diagnosis. (2011) *Annu Rev Microbiol*. 65, 501-521.
28 Manichanh, C., Borruel, N., Casellas, F., & Guarner, F., The gut microbiota in IBD. (2012) *Nat Rev Gastroenterol Hepatol*. 9, 599-608.
29 Qin, J. et al., A metagenome-wide association study of gut microbiota in type 2 diabetes. (2012) *Nature*. 490, 55-60.
30 Scher, J. U. & Abramson, S. B., The microbiome and rheumatoid arthritis. (2011) *Nat Rev Rheumatol*. 7, 569-578.
31 Henao-Mejia, J. et al., Inflammasome-mediated dysbiosis regulates progression of NAFLD and obesity. (2012) *Nature*. 482, 179-U167.
32 McCaughey, L. C. et al., Lectin-like bacteriocins from *Pseudomonas* spp. utilise D-rhamnose containing lipopolysaccharide as a cellular receptor. (2014) *PLoS Pathog*. 10, e1003898.
33 Hao, Y., King, J. D., Huszczynski, S., Kocincova, D., & Lam, J. S., Five New Genes Are Important for Common Polysaccharide Antigen Biosynthesis in *Pseudomonas aeruginosa*. (2013) *Mbio*. 4.
34 Weisner, A. M., Chart, H., Bush, A., Davies, J. C., & Pitt, T. L., Detection of antibodies to *Pseudomonas aeruginosa* in serum and oral fluid from patients with cystic fibrosis. (2007) *J Med Microbiol*. 56, 670-674.
35 Fyfe, J. A. M., Harris, G., & Govan, J. R. W., Revised Pyocin Typing Method For *Pseudomonas-Aeruginosa*. (1984) *J Clin Microbiol*. 20, 47-50.
36 Bragonzi, A., Murine models of acute and chronic lung infection with cystic fibrosis pathogens. (2010) *International Journal of Medical Microbiology*. 300, 584-593.
37 Kageyama M, Kobayashi M, Sano Y, Masaki H. (1996) Construction and characterization of pyocin-colicin chimeric proteins. *J Bacteriol*. 178(1), 103-10.

The invention claimed is:

1. A method for prophylaxis or treatment of a *Pseudomonas aeruginosa* respiratory infection in a subject wherein a therapeutically effective amount of an S-type pyocin protein is delivered to the subject by pulmonary administration.

2. The method according to claim 1 wherein the subject to be treated has, or is at risk of developing, a bacterial pneumonia.

3. The method according to claim 2 wherein the subject to be treated has compromised respiratory tract function and/or compromised immune function.

4. The method according to claim 2 wherein the subject to be treated is suffering from cystic fibrosis or chronic obstructive pulmonary disease.

5. The method according to claim 2 wherein the subject is a cancer patient or a patient affected by congestive heart failure or AIDS.

6. The method according to claim 1 wherein the subject to be treated has, or is at risk of developing, community-acquired pneumonia, ventilator-associated pneumonia or hospital-acquired pneumonia.

7. The method according to claim 1 wherein the S-type pyocin protein comprises an S2, SD2, S5 or AP41 targeting portion.

8. The method according to claim 7 wherein the pyocin protein comprises an S5 targeting portion.

9. The method according to claim 1 wherein the S-type pyocin protein comprises an S2, SD2, S5 or AP41 effector portion.

10. The method according to claim 9 wherein the S-type pyocin protein comprises an S5 effector portion.

11. The method according to claim 1 wherein the S-type pyocin protein is an SD2, SD2, S5, AP41 or L1 pyocin.

12. The method according to claim 11 wherein the S-type pyocin protein is an S5 pyocin.

13. The method according to claim 1 wherein a combination of two or more pyocin proteins is administered to the subject.

14. The method according to claim 13 wherein the combination comprises an S5 pyocin, an L1 pyocin, an S2 pyocin, an SD2 pyocin and/or an AP41 pyocin.

15. The method according to claim 14 wherein the combination comprises an L1 pyocin and an S2 pyocin; an L1 pyocin and an AP41 pyocin; an S2 pyocin and an AP41 pyocin; or an L1 pyocin, an S2 pyocin and an AP41 pyocin.

16. The method according to claim 15, wherein the combination further comprises a pyocin protein selected from the group consisting of an S5 pyocin, an SD2 pyocin and a combination of an S5 pyocin and an SD2 pyocin.

* * * * *